(12) United States Patent
Singh et al.

(10) Patent No.: US 11,344,858 B2
(45) Date of Patent: May 31, 2022

(54) MICRO-ELECTROLYSIS REACTOR FOR ULTRA FAST, OXIDANT FREE, C—C COUPLING REACTION AND SYNTHESIS OF DACLATASVIR ANALOGS THEREOF

(71) Applicant: Council of Scientific & Industrial Research, New Delhi (IN)

(72) Inventors: Ajay Kumar Singh, Telangana (IN); Srihari Pabbaraja, Telangana (IN); Subhash Ghosh, Telangana (IN); Mahajan Bhushan, Telangana (IN); Taufiqueahmed Mujawar, Telangana (IN)

(73) Assignee: Council of Scientific & Industrial Research

( * ) Notice: Subject to any disclaimer, the term of this patent is extended or adjusted under 35 U.S.C. 154(b) by 78 days.

(21) Appl. No.: 16/837,070

(22) Filed: Apr. 1, 2020

(65) Prior Publication Data
US 2020/0346182 A1    Nov. 5, 2020

(30) Foreign Application Priority Data
May 2, 2019    (IN) .............................. 201911017478

(51) Int. Cl.
*B01J 19/00*    (2006.01)
*B01J 19/02*    (2006.01)
(Continued)

(52) U.S. Cl.
CPC ........... *B01J 19/0093* (2013.01); *B01J 19/02* (2013.01); *C07D 403/14* (2013.01); *C25B 3/29* (2021.01);
(Continued)

(58) Field of Classification Search
CPC ........ B01J 19/00; B01J 19/0093; B01J 19/02; B01J 2219/00; B01J 2219/00002; B01J 2219/00027; B01J 2219/00033; B01J 2219/00049; B01J 2219/00051; B01J 2219/00162; B01J 2219/00164; B01J 2219/00166; B01J 2219/00781;
(Continued)

(56) References Cited

U.S. PATENT DOCUMENTS 6,306,277 B1    10/2001    Strangman et al.

FOREIGN PATENT DOCUMENTS

| | | |
|---|---|---|
| CN | 105753944 B | 10/2019 |
| IN | 201621000429 | 10/2017 |

(Continued)

OTHER PUBLICATIONS

Singh, et al., Direct Aryl-Aryl Coupling without Pre-Functionalization Enabled by Excessive Oxidation of Two-Electron Ag(I)/Ag(III) Catalyst, Advanced Synthesis & Catalysis, 360, 2032-2042 (2018), pp. 1-11.

(Continued)

*Primary Examiner* — Natasha E Young
(74) *Attorney, Agent, or Firm* — Belles Katz LLC

(57) ABSTRACT

The present invention relates to a continuous micro-electro-flow reactor system for ultra-fast, oxidant free, C—C coupling reaction for making symmetrical biaryls and analogs thereof. This invention further relates to the said process for preparation of antiviral drug, daclatasvir of general formula I.

10 Claims, 11 Drawing Sheets

(51) Int. Cl.
| | |
|---|---|
| C07D 403/14 | (2006.01) |
| C25B 3/29 | (2021.01) |
| C25B 11/00 | (2021.01) |
| C25B 11/02 | (2021.01) |
| C25B 11/04 | (2021.01) |

(52) U.S. Cl.
CPC .............. *C25B 11/02* (2013.01); *C25B 11/04* (2013.01); *B01J 2219/00033* (2013.01); *B01J 2219/00051* (2013.01); *B01J 2219/00162* (2013.01); *B01J 2219/00166* (2013.01); *B01J 2219/00842* (2013.01)

(58) Field of Classification Search
CPC .... B01J 2219/00783; B01J 2219/00819; B01J 2219/00835; B01J 2219/00837; B01J 2219/00842; B01J 2219/00851; B01J 2219/00853; B01J 2219/00858; B01J 2219/00889; B01J 2219/00891; B01J 2219/0095; B01J 2219/00952; B01J 2219/00954; B01J 2219/00961; B01J 2219/00963; B01J 2219/00984; C07D 403/00; C07D 403/14; C25B 3/00; C25B 3/20; C25B 3/29; C25B 9/00; C25B 9/13; C25B 9/17; C25B 11/00; C25B 11/02; C25B 11/04; C25B 11/051; C25B 11/052; C25B 11/055; C25B 11/057; C25B 11/061; C25B 11/073; C25B 11/075; C25B 11/091; C25D 3/00; C25D 3/02; C25D 3/12; C25D 3/50; C25D 3/53; C25D 3/562; C25D 5/00; C25D 5/02

See application file for complete search history.

(56) References Cited

FOREIGN PATENT DOCUMENTS

| | | | |
|---|---|---|---|
| IN | 201721000754 | 3/2019 | |
| WO | WO2016178250 A1 | 11/2016 | |
| WO | WO-2017021904 A1 * | 2/2017 | ........... C07D 403/14 |

OTHER PUBLICATIONS

Pinxterhuis, et al. Fast, Efficient and Low E-Factor One Pot Palladium-Catalyzed Cross-Coupling of (Hetero) Arenes. Angewandte Chemie International Edition, 56, 3354-3359 (2017), pp. 1-6.
Karimi, et al. Au—Pd Bimetallic Nanoparticles Supported on a High Nitrogen-Rich Ordered Mesoporous Carbon as an Efficient Catalyst for Room Temperature Ullmann Coupling of Aryl Chlorides in Aqueous Media. Chemical Communications, 54, 7155-7158 (2018), pp. 1-4.
Mondal. Recent Advancement of Ullmann-Type Coupling Reactions in the Formation of C—C Bond. ChemTexts, 2, 17 (2016), pp. 1-11.
Mahajan, et al. Synthesis of Bi(hetero)aryls Via Sequential Oxidation and Decarboxylation of Benzylamines in a Batch/Fully Automated Continuous Flow Process. European Journal of Organic Chemistry, 2018, 2831-2835, pp. 1-5.
Lv, et al. $N_2H_4$ as Traceless Mediator for Homo-and Cross-Aryl Coupling. Nature Communications, 9, 4739 (2018), pp. 1-11.
Feiz, et al. Continuous Flow Room Temperature Reductive Aqueous Homo-Coupling of Aryl Halides Using Supported Pd Catalysts. Scientific Reports, 6, 32719 (2016), pp. 1-6.
Hanafiah, et al. Global Epidemiology of Hepatitis C Virus Infection: New Estimates of Age-Specific Antibody to HCV Seroprevalence. Hepatology, 57, 1333-1342 (2013), pp. 1-10.
Shepard, et al. Global Epidemiology of Hepatitis C Virus Infection. The Lancet Infectious Diseases, 5, 558-567 (2005), pp. 1-10.
Sun, et al. Resensitizing Daclatasvir-Resistant Hepatitis C Variants by Allosteric Modulation of NS5A. Nature, 527, 245 (2015), pp. 1-15.
You, et al. Sulfur(VI) Fluoride Exchange as a Key Reaction for Synthesizing Biaryl Sulfate Core Derivatives as Potent Hepatitis C Virus NS5A Inhibitors and Their Structure-Activity Relationship Studies. RSC Advances, 8, 31803-31821 (2018), pp. 1-19.
Sambiagio, et al. Copper Catalysed Ullmann Type Chemistry: From Mechanistic Aspects to Modern Development. Chemical Society Reviews, 43, 3525-3550 (2014), pp. 1-26.
Zeng, et al. An Efficient and Recyclable Heterogeneous Palladium Catalyst Utilizing Naturally Abundant Pearl Shell Waste. Green Chemistry, 13, 350-356 (2011), pp. 1-7.
Alonso, et al. Highly Active Oxime-Derived Palladacycle Complexes for Suzuki-Miyaura and Ullmann-Type Coupling Reactions. The Journal of Organic Chemistry, 67, 5588-5594 (2002), pp. 1-7.
Khan, et al. The Palladium-Catalyzed Ullmann Cross-Coupling Reaction: A Modern Variant on a Time-Honored Process. Accounts of Chemical Research, 51, 1784-1795 (2018), pp. 1-12.
Dhital, et al. Low-Temperature Carbon-Chlorine Bond Activation by Bimetallic Gold/Palladium Alloy Nanoclusters: An Application to Ullmann Coupling. Journal of the American Chemical Society, 134, 20250-20253 (2012), pp. 1-4.
Lopes, et al. Combined Batch and Continuous Flow Procedure to the Chemo-Enzymatic Synthesis of Biaryl Moiety of Odanacatib. Journal of Molecular Catalysis B: Enzymatic, 104, 101-107 (2014), pp. 1-7.
Dalla-Vechia, et al. A Three Step Continuous Flow Synthesis of the Biaryl Unit of the HIV Protease Inhibitor Atazanavir. Organic & Biomolecular Chemistry, 11, 6806-6813 (2013), pp. 1-8.
Hansen, et al. New Ligands for Nickel Catalysis from Diverse Pharmaceutical Heterocycle Libraries. Nature Chemistry, 8, 1126 (2016), pp. 1-5.
Ghorai, et al. Bimetallic Nickel Complexes for Aniline C—H Alkylations. ACS Catalysis, 8, 11657-11662 (2018), pp. 1-6.
Li, et al. Electrochemically Enabled, Nickel-Catalyzed Amination. Angewandte Chemie International Edition, 56, 13088-13093 (2017), pp. 1-6.
Yan, et al. Synthetic Organic Electrochemical Methods Since 2000: On the Verge of a Renaissance. Chemical Reviews, 117, 13230-13319 (2017), pp. 1-162.
Jeong, et al. One-Flow Syntheses of Diverse Heterocyclic Furan Chemicals Directly from Fructose via Tandem Transformation Platform. Npg Asia Materials, 7, e173 (2015), pp. 1-8.
Sharma, et al. Odorless Isocyanide Chemistry: An Integrated Microfluidic System for a Multistep Reaction Sequence. Angewandte Chemie 125, 7712-7716 (2013), pp. 1-5.
Nadri, et al. Investigation of the Catalytic Activity of a Pd/Biphenyl-Based Phosphine System in the Ullmann Homocoupling of Aryl Bromides. Journal of Organometallic Chemistry, 696, 2966-2970 (2011), pp. 1-5.
Li, et al. New Role of $CO_2$ as a Selective Agent in Palladium-Catalyzed Reductive Ullmann Coupling with Zinc in Water. The Journal of Organic Chemistry, 68, 9867-9869 (2003), pp. 1-3.
Pinxterhuis, et al. Fast, Efficient and Low E-Factor One-Pot Palladium-Catalyzed Cross-Coupling of (Hetero)Arenes. Angewandte Chemie International Edition, 57, 9452-9455 (2018), pp. 1-4.
Buter, et al. Palladium-Catalyzed, tert-Butyllithium-Mediated Dimerization of Aryl Halides and Its Application in the Atropselective Total Synthesis of Mastigophorene A. Angewandte Chemie International Edition, 55, 3620-3624 (2016), pp. 1-5.
Masuda, et al. Aryl Ketones as Single-Electron-Transfer Photoredox Catalysts in the Nickel-Catalyzed Homocoupling of Aryl Halides. European Journal of Organic Chemistry, 2016, 5822-5825 (2016), pp. 1-4.
Schroeter, et al. Oxidative and Reductive Cross-Coupling Reactions Catalyzed by an Anionic "Ligandless" Palladium Complex. Organic Process Research & Development, 22, 1614-1621 (2018), pp. 1-8.
Zhang, et al. Synthesis and evaluation of novel potent HCV NS5A inhibitors. Bioorganic and Medicinal Chemistry Letter 22, 4864-4868, (2012), pp. 1-5.

(56) References Cited

OTHER PUBLICATIONS

Carneiro, et al. A Process Intensified Flow Synthesis of 1H-4-Substituted Imidazoles—Towards the Continuous Production of Daclatasvir. ACS Sustainable Chemistry and Engineering, 3, 3445-3453 (2015), pp. 1-25.
Ghosh, et al. Nanocrystalline Ni—Cu Alloy Plating by Pulse Electrolysis. Surface and Coatings Technology, 126, 48-63 (2000), pp. 1-16.
Cheng, et al. Visible-Light Photoredox in Homolytic Aromatic Substitution: Direct Arylation of Arenes with Aryl Halides. Organic Lett. 15, 2664-2667 (2013), pp. 1-4.
Zhou, et al. Copper-Catalyzed Cross-Coupling of Boronic Esters with Aryl Iodides and Application to the Carboboration of Alkynes and Allenes. Angew. Chem. Int. Ed. 53, 3475-3479 (2014), pp. 1-5.
Peng, et al. Palladium-Catalyzed Suzuki Cross-Coupling of Arylhydrazines via C—N Bond Cleavage J. Org. Chem. 79, 2733-2738 (2014), pp. 1-6.
Vantourout, et al. Spectroscopic Studies of the Chan-Lam Amination: A Mechanism-Inspired Solution to Boronic Ester Reactivity. J. Am. Chem. Soc. 139, 4769-4779 (2017), pp. 1-11.
Abdellatif, et al. Celecoxib Prodrugs Possessing a Diazen-1-ium-1,2-Diolate Nitric Oxide Donor Moiety: Synthesis, Biological Evaluation and Nitric Oxide Release Studies. Bioorg. Med. Chem. Lett., 20(15), 4544-4549; (2010), pp. 1-6.
Abdellatif, et al. Synthesis, Cyclooxygenase Inhibition, and Anti-Inflammatory Evaluation of Novel Diarylheterocycles with a Central Pyrazole, Pyrazoline, or Pyridine Ring. Medicinal Chemistry Research, 24, 2632-2644, 2015, pp. 1-13.

* cited by examiner

MICRO-ELECTROLYSIS REACTOR FOR ULTRA FAST, OXIDANT FREE, C—C COUPLING REACTION AND SYNTHESIS OF DACLATASVIR ANALOGS THEREOF

FIELD OF THE INVENTION

The present invention relates to a process involving continuous micro-electro-flow reactor system for ultra-fast, oxidant free, C—C coupling reactions for the synthesis of symmetrical biaryls (arenes). In particular, the invention relates to the said process for preparation of antiviral drug daclatasvir of FORMULA I.

FORMULA I

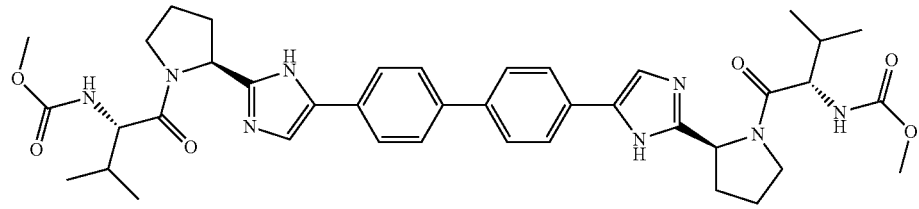

BACKGROUND OF THE INVENTION

The present invention focuses on the development of ultrafast aryl-aryl bond forming reactions which have been of great interest since a long time in the history and which find wide applications in synthesis of agrochemicals, pharmaceuticals, and natural products (*Advanced Synthesis & Catalysis*, 360, 2032-2042 (2018), *Angewandte Chemie International Edition*, 56, 3354-3359 (2017), *Chemical Communications*, 54, 7155-7158 (2018), *ChemTexts*, 2, 17 (2016), *European Journal of Organic Chemistry*, 2018, 2831-2835 (2018), *Nature Communications*, 9, 4739 (2018), *Scientific Reports*, 6, 32719 (2016)).

Worldwide more than 170 million people are infected with hepatitis C virus (HCV) *Hepatology*, 57, 1333-1342 (2013), *The Lancet Infectious Diseases*, 5, 558-567 (2005)). Daclatasvir (DCV; also known as BMS-790052 and Daklinza) belong to the family of symmetrical biaryl core moiety and mostly used in the combination therapy for the treatment of hepatitis C genotype 1, 3, or 4 infections (*Nature*, 527, 245 (2015)). World Health Organization has listed daclatasvir as one of the essential medicines for the human health system. (*RSC Advances*, 8, 31803-31821 (2018)).

Symmetrical biaryls are conventionally prepared through the Ullmann homocoupling of aryl halide with excess of copper or Pd catalyst under heating conditions (>200° C.) (*Chemical Society Reviews*, 43, 3525-3550 (2014), *ChemTexts*, 2, 17 (2016), *Green Chemistry*, 13, 350-356 (2011), *The Journal of Organic Chemistry*, 67, 5588-5594 (2002)). During recent years, scientists and engineers have been working in the direction towards the development of more efficient catalyst systems that use single or bimetallic transition metal combinations of Pd, Ni, and Au, under both homogeneous and heterogeneous conditions (*Accounts of Chemical Research*, 51, 1784-1795 (2018), *Journal of the American Chemical Society*, 134, 20250-20253 (2012), *Nature Communications*, 9, 4739 (2018), *Journal of Molecular Catalysis B: Enzymatic*, 104, 101-107 (2014), *Organic & Biomolecular Chemistry*, 11, 6806-6813 (2013)).

Among the novel metal catalysts (Pd, Ir, Ru, Rh, Pt), nickel catalysts are inexpensive and exhibit high reactivity towards less reactive electrophiles such as aryl bromide/chloride, thus offering an alternative approach to palladium (*Nature Chemistry*, 8, 1126 (2016), *Nature Communications*, 9, 4739 (2018)). Although, a large number of batch protocols for the synthesis of symmetrical and unsymmetrical biaryls already exists, most of them involve higher temperatures (up to 140° C.), utilize excess unwanted bases, additional oxidants (to change the low valent nickel species to high valent in same pot). Also, the insufficient reactant collision results in longer reaction times (4-48 h) to complete the reaction (*Chemical Society Reviews*, 43, 3525-3550 (2014), *ChemTexts*, 2, 17 (2016), *Green Chemistry*, 13, 350-356 (2011), *The Journal of Organic Chemistry*, 67, 5588-5594 (2002)). To reduce the oxidant wastage in chemical reaction, electrochemistry represents the most suitable electron transfer process where solid surface cathode or anode directly interacts with catalyst and changes the oxidation state (*ACS Catalysis*, 8, 11657-11662 (2018), *Angewandte Chemie International Edition*, 56, 13088-13093 (2017), *Chemical Reviews*, 117, 13230-13319 (2017)). Simultaneously, electrochemistry a surface phenomenon also enables the unique activation of reagents enabling selectivity and transformations which are not possible by other techniques. Batch process reactions have low surface to volume ratio and inefficient mixing results in the longer reaction times to complete the reaction with off quality product and is inappropriate for the automation. It is still challenging to demonstrate a high surface area, reducing the distance between electrodes for more efficient electron transfer chemistry with excellent performance.

To realize the concept of redox electrochemistry for coupling reaction and ultra-fast daclatasvir synthesis, an emerging technology so-called continuous-flow microfluidic device is an efficient synthetic tool which can overcome the issues related to batch processes with an attractive advantage such as an excellent mass transfer and also we can maximize the potential of the surface phenomenon properties i.e. reduce the distance between the electrodes for more efficient electron transfer, high surface-to-volume ratio, which leads to an enrichment in the selectivity and a reduction in reaction time (*Npg Asia Materials*, 7, e173 (2015); *Angewandte Chemie* 125, 7712-7716 (2013)). However, to the best of our knowledge there are no reports on the patterned electrode-posited Ni/Pt metal over the copper plates in a microreactor for the ultra-fast Ullmann coupling and further extend process for the multi-step continuous synthesis of daclatasvir active pharmaceutical ingredient (API). In general, traditional macro reactor (Batch process) method requires several days to produce daclatasvir API (PCT Int. Appl. (2016), WO 2016178250 A1 20161110, Faming Zhuanli Shenqing (2016), CN 105753944 A 20160713, Indian Pat.

Appl. (2017), IN 201621000429 A 20171020, Indian Pat. Appl. (2019), IN 201721000754 A 20190315.

OBJECTIVE OF THE INVENTION

In view of the limitations in the prior art, the main objective of the present invention is to provide a continuous micro-electro-flow reactor system for ultra-fast Ullmann coupling to obtain biaryls and analogs thereof.

Another objective of the present invention is to provide a process that can be carried out in continuous flow multi-step process system for preparation of daclatasvir, an anti-viral drug.

SUMMARY OF THE INVENTION

Aiming to overcome the defects and limitations in the prior-art, we have developed an ultra-fast fully continuous flow process for the preparation of daclatasvir of formula I.

Formula I

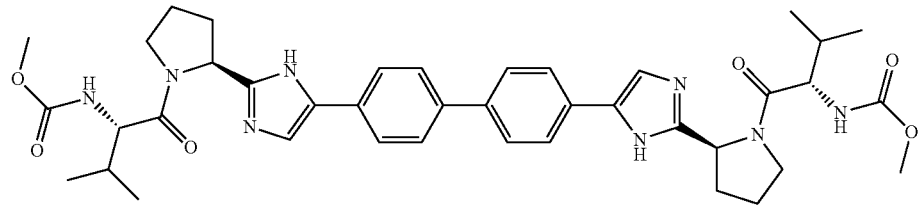

In one embodiment, the present invention provides, a process using a continuous micro-electro-flow reactor (μ-EFR) system for the preparation of daclatasvir of formula I.

In another embodiment, the continuous micro-electro-flow reactor comprise of a long-serpentine tunnel sandwiched in a solid block of a graphite and metal anode and three alternate polytetrafluoroethylene (PTFE) sheets with the identical dimension of groove channels sandwiched between two metal holders tightly pressed by the screw to seal the device for leaks.

In a preferred embodiment, the middle part of the serpentine patterned anode comprises of an assembly of copper plate support micro-patterned with inorganic nanoparticles; wherein, the inorganic nanoparticles comprise nickel nanoparticles, platinum nanoparticles or both metal nanoparticles combined together, wherein, the inorganic nanoparticles have an average size in the range of 10-100 nm and thickness of 4 μM.

In one embodiment, the present invention provides an improved process for the synthesis of daclatasvir comprising the steps of:

a) introducing a solution of a haloarene of Formula 1 and a Ni catalyst of Formula 2 in an aprotic solvent to a continuous micro-electro flow reactor and maintaining the reaction mixture in the reactor for about 1-200 minutes at a temperature of about 25-80° C. and at a pressure of about 0-5 bar to obtain compounds of Formula 3a-3h.

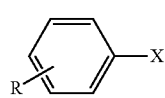

(1)

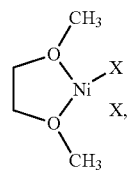

(2)

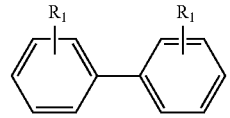

(3a-3h)

Representative compounds of Formula 1 are: bromobenzene (1a); chlorobenzene (1a'); 1-bromo-4-methylbenzene (1b); 1-chloro-4-methylbenzene (1b'); 1-bromo-3-methylbenzene (1c); 1-chloro-3-methylbenzene (1c'); 1-bromonaphthalene (1d); 1-chloronaphthalene (1d'); 2-bromonaphthalene (1e); 2-chloronaphthalene (1e'); 4-bromo-1,1'-biphenyl (1f); 4-chloro-1,1'-biphenyl (1f'); 2-(4-bromophenyl)-2-methyl-1,3-dioxolane (1g); 1-(4-bromophenyl)ethanone (1h).

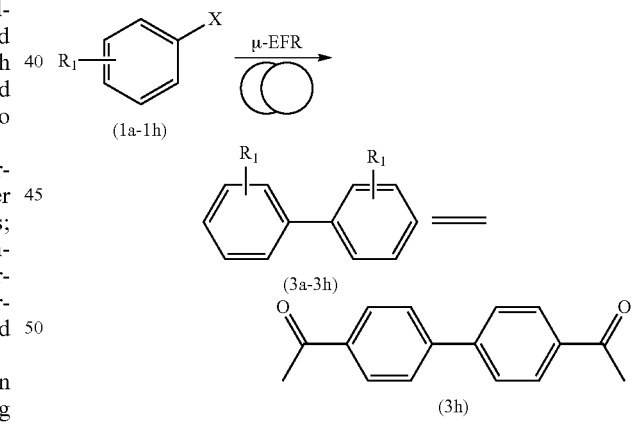

The represented compound of Formula 3 is: 1,1'-biphenyl (3a); 4,4'-dimethyl-1,1'-biphenyl (3b); 3,3'-dimethyl-1,1'-biphenyl (3c); 1,1'-binaphthalene (3d); 2,2'-binaphthalene (3e); 1,1':4',1":4",1'''-quaterphenyl (30; 4,4'-bis(2-methyl-1,3-dioxolan-2-yl)-1,1'-biphenyl (3g); 1,1'-([1,1'-biphenyl]-4,4'-diyl) diethanone (3h).

b) Pumping a solution of reactants of formula 3h and a brominating agent in an aprotic solvent into the continuous micro-electro-flow reactor; maintaining the reaction mixture in a reactor for about 10-200 minutes at a temperature of about 30-50° C. and at a pressure of about 1-10 bar for the synthesis of a compound of formula 4; Removal of the organic solvents to obtain the compound of formula 4;

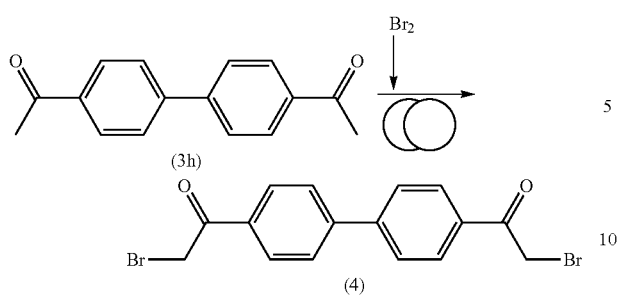

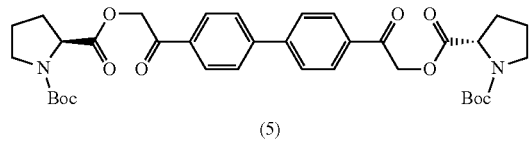

c) Ester formation step; the suspension of formula 4 and the N-protected-L-proline are dissolved in an aprotic solvent and separately base is dissolved in a protic solvent and both the solutions are pumped through the continuous micro-electro-flow reactor; maintaining the reaction mixture in reactor for about 1-5 minutes at a temperature of about 30-80° C. and at a pressure about 1-10 bar to obtain a compound of formula 5.

d) Cyclization step; the crude mixture 5 is directly pumped along with ammonium acetate in protic solvent through T junction into the SS-tubing of the continuous micro-electro-flow reactor at 130-180° C. for about 1-5 minutes at 10-30 bar for the synthesis of the compound of formula 6. The processed outflowing mixture comes out as a two-phase aqueous-organic solution. The aqueous phase was separated and discarded, and the solvent from the organic phase was evaporated under reduced pressure. The crude product was dissolved in ethyl acetate and extracted into 1 M HCl. Neutralization with NaHCO$_3$ and re-extraction into ethyl acetate provided the imidazole compound of formula 6 after drying with Na$_2$SO$_4$ and evaporation of the solvent.

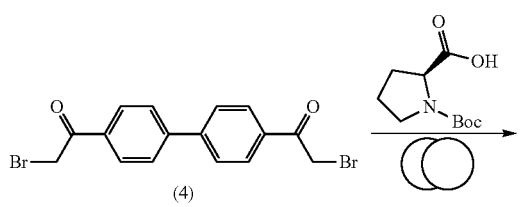

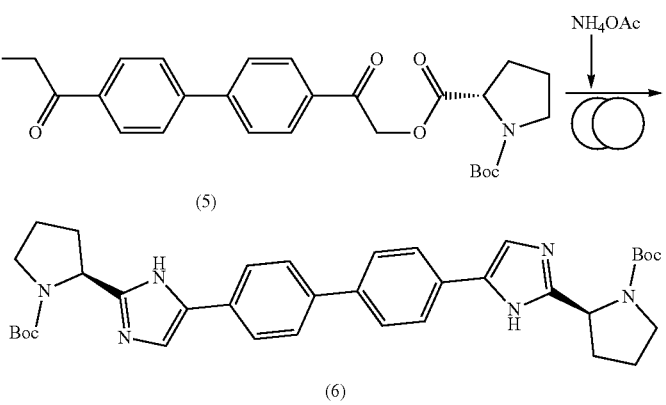

e) In deprotection step, a solution of reactants of formula 6 and aqueous HCl in a protic solvent are pumped into the continuous micro-electro-flow reactor; maintaining the reaction mixture in reactor for about 1-5 minutes at a temperature of about 20-40° C. and at a pressure of about 1-10 bar followed by the process known in the prior art for extraction and isolation of a compound of formula 7.

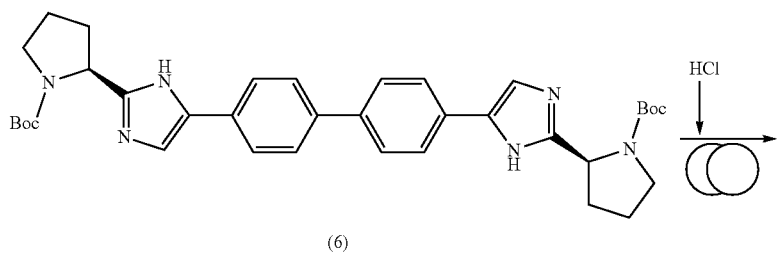

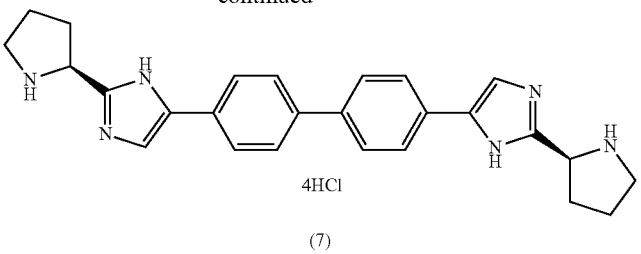

(7)

In final step, pumping a solution of reactants of formula 7, Moc-L-valine, base such as DIPEA or TEA, HOBt, and EDC.HCl and coupling agent in a polar aprotic solvent into the continuous micro-electro-flow reactor; maintaining the reaction mixture in reactor for about 20-100 minutes at a temperature of about 20-40° C. and at a pressure of about 1-10 bar followed by the extraction and removing organic solvents to obtain daclatasvir of formula I.

FIG. 6 shows to make align the patterns, the 4-corners of each two teflon film were drilled to make a hole (1 mm diameter). Thereafter, a both the electrodes were merged by teflon zig-zag channel sheets with identical dimension to fit groove channels and coupled to each other by inserting metal pins through the holes at the film corners.

FIG. 7 shown to patterning of Ni electro-plating over the copper plates: Ni nanoparticles were patterned over copper

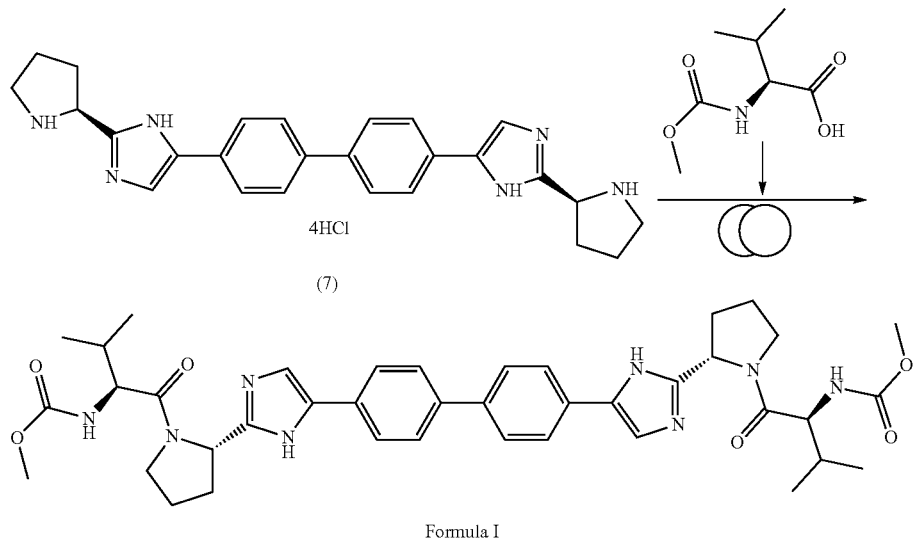

BRIEF DESCRIPTION OF DRAWINGS

Scheme 1: Illustrates the continuous-flow process system for the multi-step synthesis of daclatasvir formula (I).

plate made by electrodeposition method as reported. In this method, copper plate was cleaned by acetic acid, followed by deionized water to remove oxidized layer and dried by $N_2$ flow. Then, the copper plate was sandwiched between the above designed reactor and connected with pump. Copper plate was connected with negative charge and graphite plate connected with positive charge. Finally, Ni.acetate.$H_2$O in water solution was passed continuously through the microreactor channel. The Ni salt solution, was passed through a merged channel under the 2V of the electrode potential and with varied flow rate and temperature.

Figure 8:
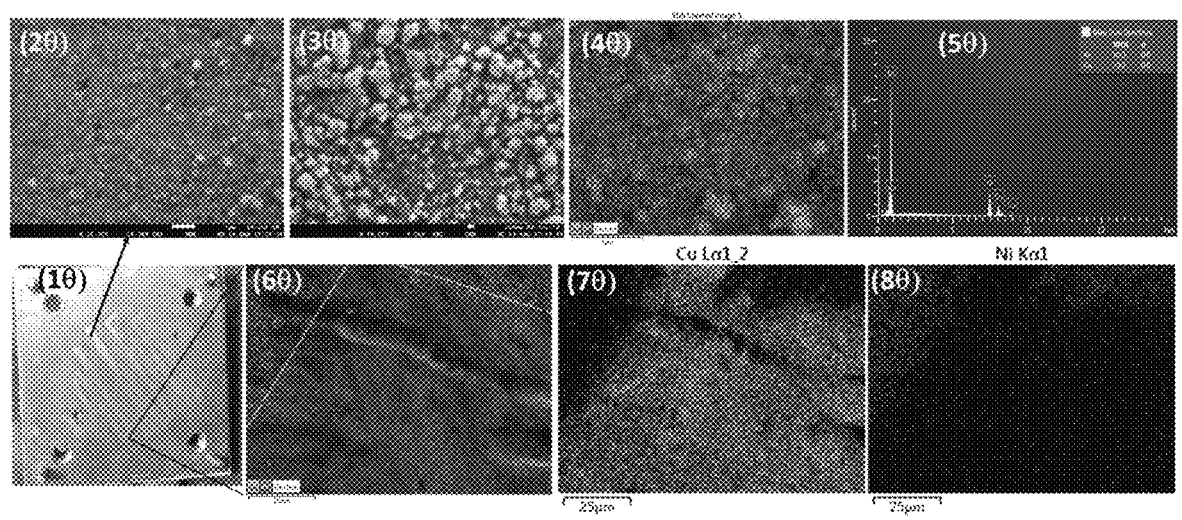

FIG. 8 illustrates the generation of a silver colored nickel nanoparticle patterning. Nanoparticle deposition was confirmed by characteristic SEM/EDX/mapping analysis.

Figure 9:
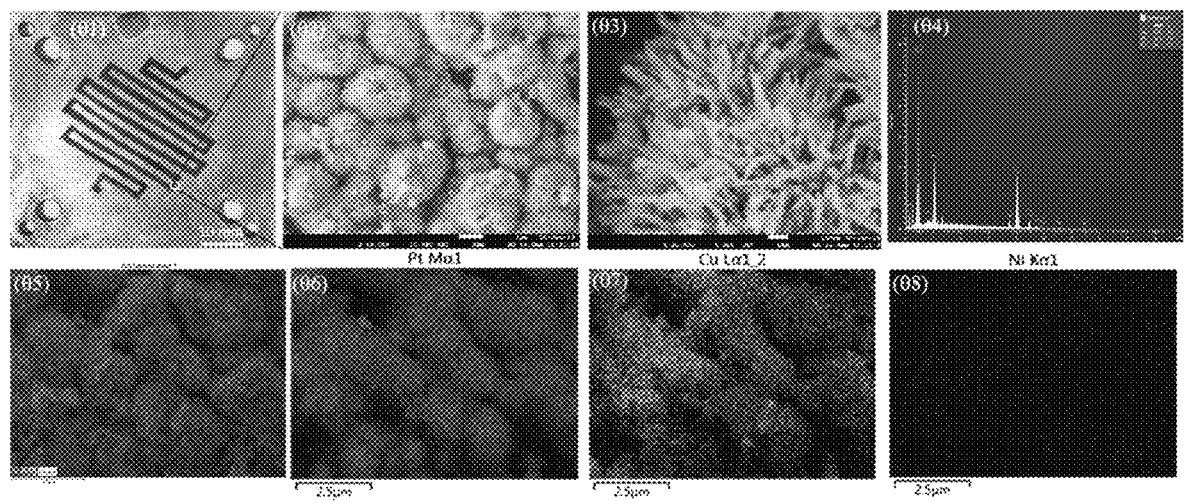

FIG. 9 shown to make platinum nanoparticle deposition over the Ni coated copper surface. Modified phosphates bath-based methods have been used to deposition of Pt over the Ni nano-particle. (U.S. Pat. No. 6,306,277 B1) Stock electrolytic solution contains mixture of Pt(IV) chlorides, diammonium hydrogen phosphate $(NH_4)_2HPO_4$, disodium hydrogen phosphate $(Na)_2HPO_4$, ammonium chloride, and water. The stock solution, was pumped with varied flow rate for varied time at various temperatures under varied current density. Generation of a black colored patterning, and nanoparticle deposition was confirmed by characteristic SEM/EDX/mapping analysis.

Figure 10:
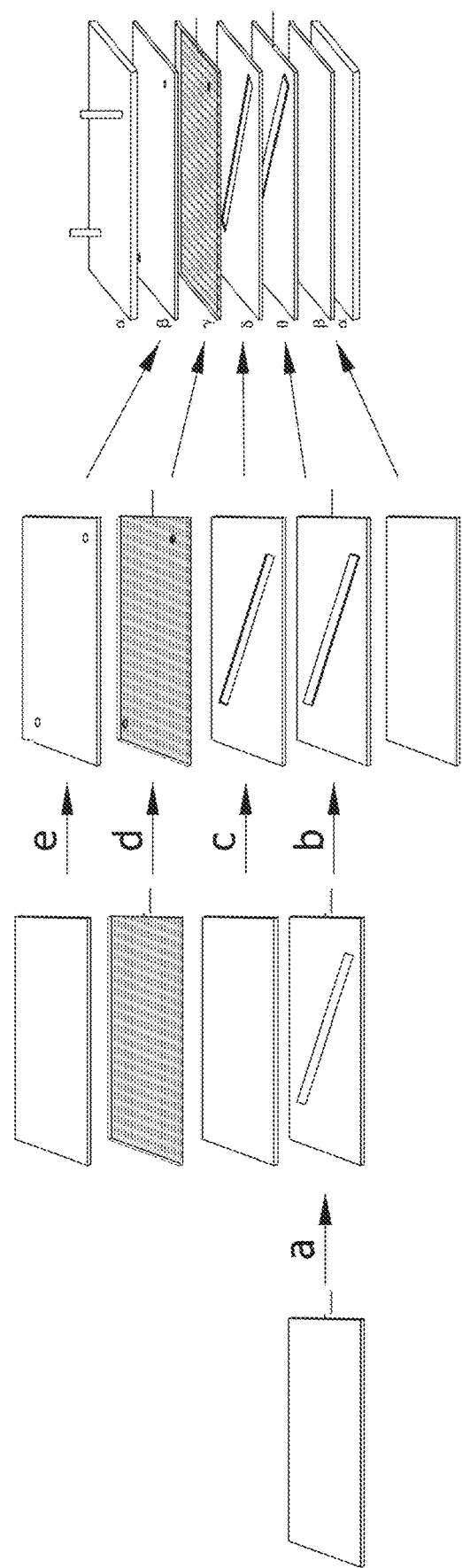

FIG. 10: Schematic design of the electro-flow reactor; (a) Cu plate coating with Ni through the electrolysis process; (b) Pt coating over the Ni Nano-particle; (c) Laser grooved PTFE channel; (d) Customised graphite electrode; (e) Laser cutted PTFE sheet.

Figure 11:
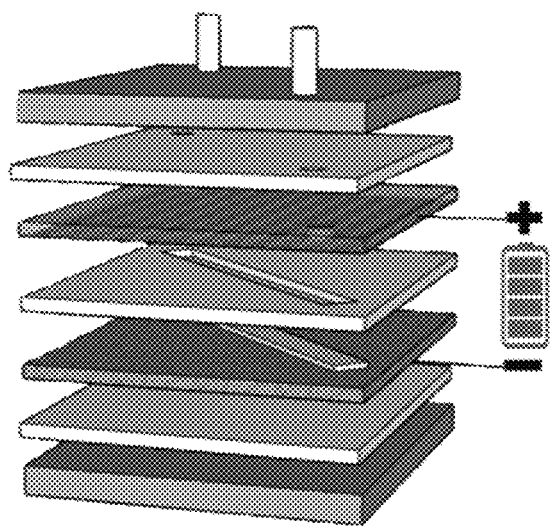

FIG. 11 illustrates a continuous micro-electro-flow reactor.

Figure 12:
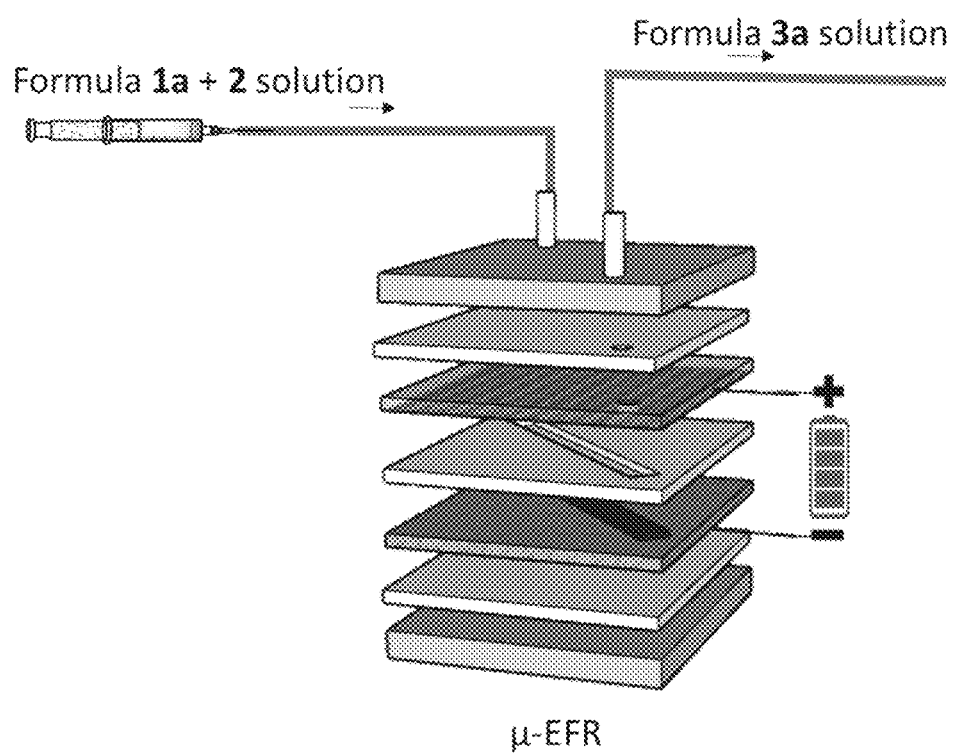

FIG. 12 illustrates introduction of a solution of formula 1, $NiCl_2 \cdot glyme$, LiCl in solvent (0.16 m) into the newly designed electro-flow reactor with a using pump.

DETAILED DESCRIPTION OF THE INVENTION

The present invention relates to a process involving continuous micro-electro-flow reactor system for ultra-fast, oxidant free, C—C coupling reactions for the synthesis of symmetrical biaryls (arenes). In particular, the invention relates to the said process for preparation of antiviral drug daclatasvir of FORMULA I.

to modify a single number, the term "about" may refer to ±10% of the said number including the indicated number. For example, "about 10%" may cover a range of 9% to 11%, and "about 1" means from 0.9-1.1.

As used herein, the term "reduced pressure" refers to a pressure that is less than atmospheric pressure. For example, the reduced pressure is about 1 mbar to about 50 mbar.

As used herein, the term "pump" refers to a device that moves fluids (liquids or gases) or sometimes slurries, by mechanical action.

As used herein, the term "protic solvents" refers to any organic solvent that contains a labile $H^+$.

As used herein, the term "protic acid" refers to any reagent that contains a labile $H^+$.

As used herein, the term "base" refers to any reagent that contains a labile $OH^-$ or proton acceptor.

In first embodiment, the present invention provides a continuous flow process for the preparation of arenes of formula 3a-3h and daclatasvir of formula I.

FORMULA I

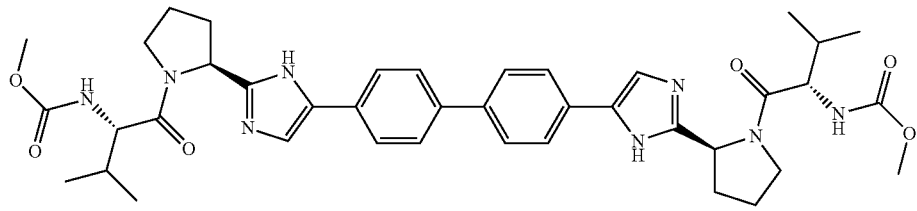

As discussed earlier, the processes described in the prior-art are mostly batch processes and have significant disadvantages. In contrast to the prior art processes, the present

FORMULA I

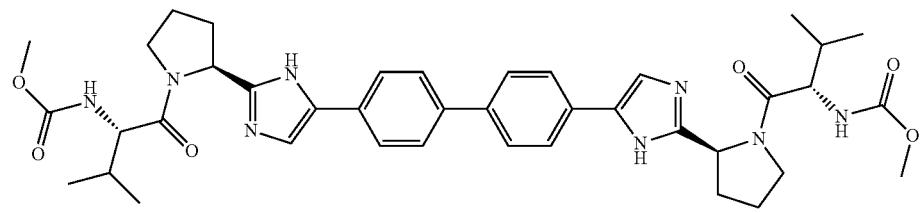

invention provides efficient, improved, simple, economical and scalable new processes by amalgamating electrochemistry and microfluidics platforms to enable the selective generation of arenes of formula 3a-3h, and further to continuous flow synthesis of antiviral daclatasvir dihydrochloride salt.

As used herein, the modifier "about" should be considered as disclosing the range defined by the absolute values of the two endpoints. For example, the expression "from about 1 to about 4" also discloses the range "from 1 to 4." When used In another embodiment, the present invention provides, a process using a continuous micro-electro-flow reactor (μ-EFR) system for the preparation of arenes of formula 3a-3h and daclatasvir of formula I.

In yet another embodiment, the continuous micro-electro-flow reactor (FIG. 11) comprise of a long-serpentine tunnel sandwiched in a solid block of a graphite and metal anode and three alternate polytetrafluoroethylene (PTFE) sheets with the identical dimension of groove channels sandwiched between two metal holders tightly pressed by the screw to seal the device for leaks.

In a preferred embodiment, the middle part of the serpentine patterned anode comprises of an assembly of copper plate anode support micro-patterned with inorganic nanoparticles; wherein, the inorganic nanoparticles comprise nickel nanoparticles, platinum nanoparticles or both metal nanoparticles combined together, wherein, the inorganic nanoparticles (Ni, Pt@Ni) have an average size in the range of 10-100 nm and electroplated thickness of 4-100 µM.

In one embodiment, the present invention provides an improved process for the synthesis of daclatasvir comprising the steps of:

Step a) introducing a solution of a haloarene of Formula 1 and a Ni catalyst of Formula 2 (X: Br, Cl) in an aprotic solvent to a continuous micro-electro flow reactor and maintaining the reaction mixture in the reactor for about 1-200 minutes at a temperature of about 25-80° C. and at a pressure of about 0-5 bar to obtain compounds of Formula 3a-3h.

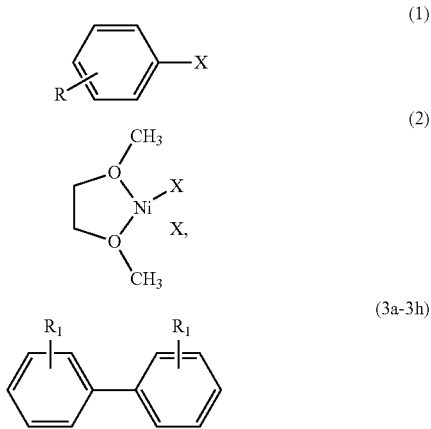

In an embodiment, the present invention provides that in step a) a reacting compound of formula 1 reacts with a compound of formula 2 in presence of various combinations of electrodes, wherein, the electrode is selected from the group consisting of Ni@Cu, Pt@Ni@Cu, Graphite, and Cu.

In one embodiment, the representative compounds of Formula 1 are: bromobenzene (1a); chlorobenzene (1a'); 1-bromo-4-methylbenzene (1b); 1-chloro-4-methylbenzene (1b'); 1-bromo-3-methylbenzene (1c); 1-chloro-3-methylbenzene (1c'); 1-bromonaphthalene (1d); 1-chloronaphthalene (1d'); 2-bromonaphthalene (1e); 2-chloronaphthalene (1e'); 4-bromo-1,1'-biphenyl (1Ο; 4-chloro-1,1'-biphenyl (1f'); 2-(4-bromophenyl)-2-methyl-1,3-dioxolane (1g); 1-(4-bromophenyl) ethanone (1h).

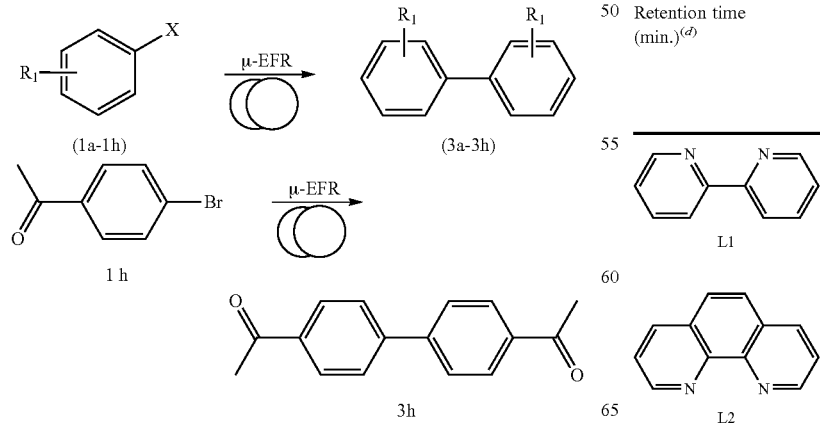

In one embodiment, the representative compound of Formula 3 is: 1,1'-biphenyl (3a); 4,4'-dimethyl-1,1'-biphenyl (3b); 3,3'-dimethyl-1,1'-biphenyl (3c); 1,1'-binaphthalene (3d); 2,2'-binaphthalene (3e); 1,1':4',1":4",1'''-quaterphenyl (30; 4,4'-bis(2-methyl-1,3-dioxolan-2-yl)-1,1'-biphenyl (3g); 1,1'-([1,1'-biphenyl]-4,4'-diyl) diethanone (3h).

In one embodiment, the solvent for the reaction in step a) is polar aprotic solvent selected from the group consisting of acetonitrile, dichloromethane, dicholoroethane, tetrahydrofuran, ethyl acetate, isopropyl acetate, dimethylformamide, dimethyl sulfoxide, acetone, N-Methylpyrrolidone, and mixtures thereof.

Table 1 represents the optimization of the model reaction of step a) with micro-electro flow reactor and in general, reaction performance was found to be dependent on the electrode, flow rate (residence time), solvent, ligand, and the concentrations of catalyst. After studying several reaction conditions, finally 98% yield of 3a (5.5 mmol h$^{-1}$ productivity Table 1, entry 6) was obtained in 4 min RT and 4 mA current (optimized conditions).

TABLE 1

Optimization of C-C coupling in continuous electro-flow process.

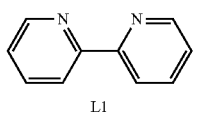

| Conditions | Entry | Deviation from above | Yield$^f$ |
|---|---|---|---|
| Effect of electrode Anode (-)$^{(a)}$ | 1 | Ni/C | 05 |
| | 2 | Ni Foam/C | 0 |
| | 3 | Cu/C | 0 |
| | 4 | Pt/C | Trace |
| | 5 | C/C | 0 |
| | 6 | Pt@Ni@Cu/C | 98 |
| Effect of Solvent$^{(b)}$ | 7 | DMA | 98 |
| | 8 | DMF | 87 |
| | 9 | MeCN | 5 |
| | 10 | THF | Trace |
| | 11 | DMSO | 34 |
| | 12 | DMA/H$_2$O (9:1) | Trace |
| Effect of ligand$^{(c)}$ | 13 | L1 | 98 |
| | 14 | L2 | 20 |
| | 15 | L3 | Trace |
| | 16 | L4 | 60 |
| | 17 | L5 | Trace |
| | 18 | NA | No reaction |
| Retention time (min.)$^{(d)}$ | 19 | 1 | 73 |
| | 20 | 2 | 77 |
| | 21 | 4 | 98 |
| | 22 | 10 | 98 |
| | 23 | 0.5 | 25 |

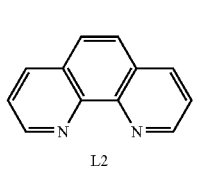

TABLE 1-continued

Optimization of C-C coupling in continuous electro-flow process.

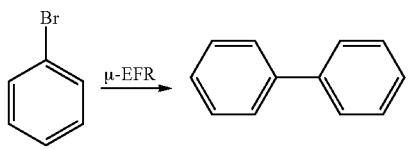

| Conditions | Entry | Deviation from above | Yield[f] |
|---|---|---|---|

L3

L4

EDTA
L5

Reaction condition:
bromobenzene (0.15 mmol), $NiCl_2 \cdot$glyme (10 mol %), bipyridine (10 mol %), LiCl (4 eq.), DMA 0.01M, current (4 mA), reaction time 4 min.
[a]various anode;

TABLE 1-continued

Optimization of C-C coupling in continuous electro-flow process.

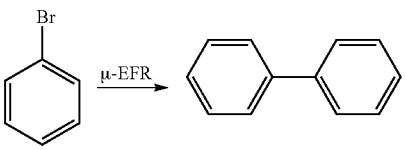 [SMILES: Brc1ccccc1 ; c1ccc(-c2ccccc2)cc1]

| Conditions | Entry | Deviation from above | Yield[f] |
|---|---|---|---|

[b]anode (Pt@Ni@Cu);
[c]ligand (10 mol %), anode (Pt@Ni@Cu),
[d]anode (Pt@Ni@Cu), reaction time varied.;
[e]bromobenzene (0.15 mmol), $NiCl_2 \cdot$Glyme (10 mol %), ligand (10 mol %), LiCl (4 eq.), DMA 1 ml, 4 mA current, anode (Pt@Ni@Cu), reaction time 4 min.;
Yield is based on GC-Mass analysis with anisol as internal standard.

Table 2 is an illustration to demonstrate comparative data between reactions reported using batch process for synthesis and current micro-electro flow reactor based method. When results were compared with previously reported literature in a conventional batch process, it's worth to mentioning here that batch process need a long reaction time 24 h with noble metal Pd catalyst, unnecessary base ($K_2CO_3$), and high temperature (100° C.) (*Journal of Organometallic Chemistry*, 696, 2966-2970 (2011)). This ultra-fast reaction was possible only because of micro-electrolysis flow reactor (μ-EFR) in combination with Pt@Ni@Cu anode bearing additional power of surface phenonmenon and electronic effect.

TABLE 2

Comparative results for the products synthesized from the electrolysis reactor.

| Entry | Substrate formula (1) | Product formula (3) | Comparative result |
|---|---|---|---|
| 1 | 1a (PhBr) | 3a (biphenyl) | [Ni] 98%, rt, 4 min (our study) ([Pd] 100%, 100° C., $K_2CO_3$ base, 24 h) *Journal of Organometallic Chemistry*, 696, 2966-2970 (2011) (Pd/C, Zn, $CO_2$, 91%, 15 hr) *The Journal of Organic Chemistry*, 68, 9867-9869 (2003) |
| 2 | 1a' (PhCl) | 3a' (biphenyl) | [Ni] 90%, rt, 4 min (our study) (Pd/C, Zn, $CO_2$, 96%, 36 h) *The Journal of Organic Chemistry*, 68, 9867-9869 (2003) |
| 3 | 1b (4-Me-C6H4-Br) | 3b (4,4'-dimethylbiphenyl) | [Ni] 91%, rt, 4 min |
| 4 | 1b' (4-Me-C6H4-Cl) | 3b' (4,4'-dimethylbiphenyl) | [Ni] 88%, rt, 4 min, |
| 5 | 1c (3-Me-C6H4-Br) | 3c (3,3'-dimethylbiphenyl) | [Ni] 90%, rt, 4 min |

TABLE 2-continued

Comparative results for the products synthesized from the electrolysis reactor.

| Entry | Substrate formula (1) | Product formula (3) | Comparative result |
|---|---|---|---|
| 6 | 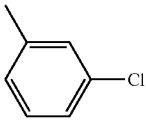<br>1c' | 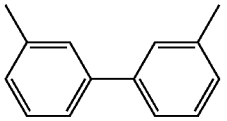<br>3c' | [Ni] 76%, rt, 4 min |
| 7 | 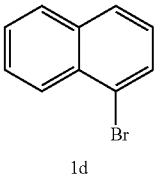 [SMILES: Brc1cccc2ccccc12]<br>1d | 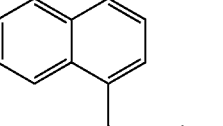<br>3d | [Ni] 74%, rt, 4 min (our study)<br>(Pd-PEOOSI-IPr,t-BuLi, 92%, 10 min)<br>*Angewandte Chemie International Edition*, 57, 9452-9455 (2018) |
| 8 | 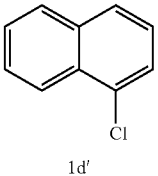 [SMILES: Clc1cccc2ccccc12]<br>1d' | 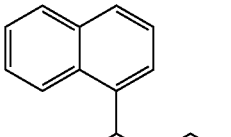<br>3d' | [Ni] 65%, rt, 4 min (our study)<br>(Pd-PEOOSI IPr, 62%, 1 h) *Angewandte Chemie International Edition*, 55, 3620-3624 (2016)<br>(Pd/C, Zn, $CO_2$, 36 hr, 95%) *The Journal of Organic Chemistry*, 68, 9867-9869 (2003) |
| 9 | 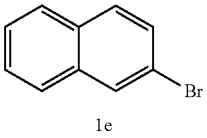<br>1e | 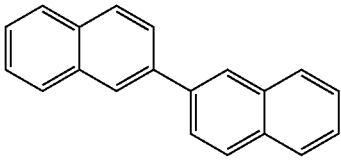<br>3e | [Ni] 65%, rt, 4 min (our study)<br>(Pd-PEOOSI IPr, 62%, 1 h)<br>*Angewandte Chemie International Edition*, 55, 3620-3624 (2016) |
| 10 | 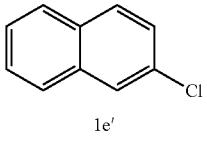 [SMILES: Clc1ccc2ccccc2c1]<br>1e' | 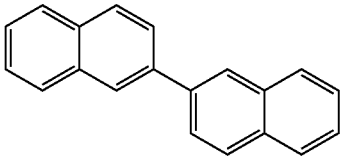<br>3e' | [Ni] 65%, rt, 4 min (our study)<br>(Pd-PEOOSI IPr, 62%, 1 h)<br>*Angewandte Chemie International Edition*, 55, 3620-3624 (2016) |
| 11 | 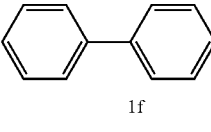<br>1f | 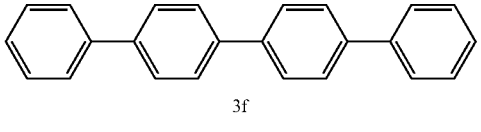 [SMILES: c1ccc(-c2ccc(-c3ccc(-c4ccccc4)cc3)cc2)cc1]<br>3f | [Ni] 72%, rt, 4 min (our study)<br>(hυ(CFL) [NiCl$_2$(dtbbpy)] NEtiPr$_2$, 79%, 12 h)<br>*European Journal of Organic Chemistry*, 2016, 5822-5825 (2016) |
| 12 | 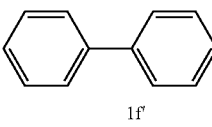<br>1f' | 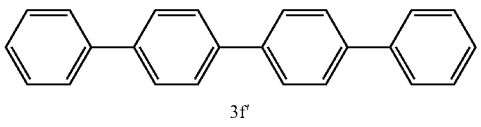 [SMILES: c1ccc(-c2ccc(-c3ccc(-c4ccccc4)cc3)cc2)cc1]<br>3f' | [Ni] 67%, rt, 4 min |

TABLE 2-continued

Comparative results for the products synthesized from the electrolysis reactor.

| Entry | Substrate formula (1) | Product formula (3) | Comparative result |
|---|---|---|---|
| 13 | 1g | 3g | [Ni] 89%, rt, 4 min |
| 14 | 1h | 3h | [Ni] 92%, rt, 200 min (our study) ([Pd], HQ, $K_3PO_4$, 140° C., 24 h, 87%) Organic Process Research & Development, 22, 1614-1621 (2018) |

[a] Yields are based on isolated yields.

Step b) Pumping a solution of reactants of formula 3h and a brominating agent in an aprotic solvent into the continuous micro-electro-flow reactor; maintaining the reaction mixture in reactor for about 10-200 minutes at a temperature of about 30-50° C. and at a pressure of about 1-10 bar for the synthesis of a compound of formula 4; removal of the organic solvents to obtain the compound of formula 4;

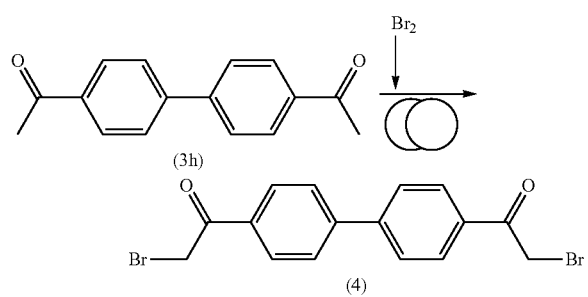

Table 3 illustrates the reaction optimization conditions for the continuous manufacturing platform to produce on-demand medicinally privileged daclatasvir intermediate formula 4 with excellent yield (93%) in residence time 78.5 min. In general, batch process requires 16 hours for the reaction to complete with moderate yield (87%) (Bioorganic and Medicinal Chemistry Letter 22, 4864-4868, (2012)).

TABLE 3

Reaction optimization for the bromination of formula 4.

| | Flow rate (μL/min) | | Retention time | |
|---|---|---|---|---|
| Entry | Formula 3h | $Br_2$ | (min.) | % Yield of 4 |
| $1^a$ | 200 | 200 | 39.2 | 53 |
| $2^b$ | 10 | 10 | 78.5 | 93 |
| $3^b$ | 100 | 100 | 78.5 | 93 |

Solution concentration: (a) Formula 3h (0.05M in DCM);
$Br_2$ concentration (0.1M in DCM);
(b) Formula 3h (0.01M in DCM);
$Br_2$ concentration (0.02M in DCM), yields are based on LC-MS.

In one embodiment, the compound of formula 3h continuously react with brominating agent in presence of a Lewis acid and solvent, wherein the brominating agent is selected from the group consisting of bromine, boron tribromide, phosphorus tribromide, carbon tetrabromide, N-bromoacetamide, N-bromophthalimide, N-bromosuccinimide, bromotrichloromethane, pyridinium tribromide, tetrabutylammonium tribromide, trimethylphenylammonium tribromide, benzyltrimethyl ammoniumtribromide, bromodimethylsulfonium bromide, 1-butyl-3-methylimidazolium tribromide, 1,2-dibromo-1,1,2,2-tetrachloroethane, 4-dimethylaminopyridinium bromide, 2,4,4,6-tetrabromo-2, 5-cyclohexadienone, and mixtures thereof; and Lewis acid is selected from the group consisting of $BF_3$, $MgBr_2$, $SnCl_4$, $TiCl_4$, $FeCl_3$, $AlCl_3$, $MeAlCl_2$, $Me_2AlCl$, $LiClO_4$, and mixtures thereof and the solvent is a polar aprotic solvent selected from the group consisting of acetonitrile, dichloromethane, dicholoroethane, tetrahydrofuran, ethyl acetate, isopropyl acetate, dimethylformamide, dimethyl sulfoxide, acetone, N-Methylpyrrolidone, and mixtures thereof.

Step c) Ester formation step: the suspension of formula 4 and the N-protected-L-proline were dissolved in an aprotic solvent and separately base was dissolved in a protic solvent and both the solutions were pumped through the continuous micro-electro-flow reactor; maintaining the reaction mixture in reactor for about 1-5 minutes at a temperature of about 30-80° C. and at a pressure about 1-10 bar to obtain a compound of formula 5.

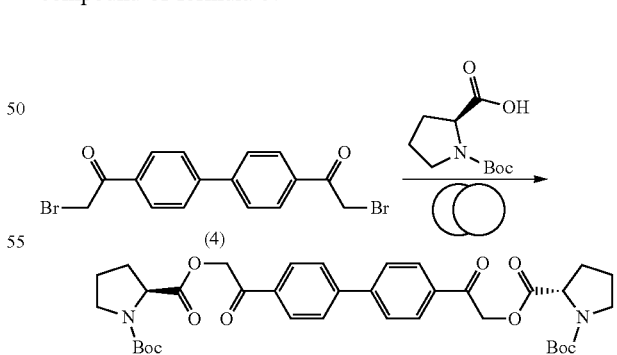

This continuous manufacturing platform produces on-demand medicinally privileged daclatasvir intermediate 5 with excellent yields within 2.5 min of residence time, while macro-reactor need 3 hours to complete the reaction (Table 4).

TABLE 4

Reaction optimization for the proline coupling to get 1j.

| Entry | Flow rate (ml/min) Formula 4 sol. | Flow rate (ml/min) Base | Stoichiometric ratio (Formula 4:Base) | Retention time (min) | % Yield of 5 |
|---|---|---|---|---|---|
| 1 | 1.0 | 3.0 | 1:14.4 | 2.5 | 49 |
| 2 | 1.5 | 2.5 | 1:8 | 2.5 | 52 |
| 3 | 2.0 | 2.0 | 1:4.8 | 2.5 | 60 |
| 4 | 3.0 | 1.0 | 1:1.6 | 2.5 | 72 |

Reaction condition: 4 solutions (0.25M) and the N-boc-L-proline (0.26M) in MeCN;
triethylamine (1.2M) in MeCN;
Yield are based on LC-MS.

In one embodiment, the reaction of compound of formula 4 with N-Protected-L-proline is performed in the presence of a base and a solvent, wherein, the base is selected from the group consisting of trimethylamine, sodium hydroxide, potassium hydroxide, sodium methoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, piperidine, pyridine and mixtures thereof and the solvent is polar aprotic solvent selected from the group consisting of acetonitrile, dichloromethane, dicholoroethane, tetrahydrofuran, ethyl acetate, isopropyl acetate, dimethylformamide, dimethyl sulfoxide, acetone, N-Methylpyrrolidone, and mixtures thereof.

Step d) Cyclization step: the crude mixture 5 was directly pumped along with a reagent in a protic solvent through T junction into the SS-tubing of the continuous micro-electro-flow reactor at 130-180° C. for about 1-5 minutes at 10-30 bar for the synthesis of the compound of formula 6. The processed outflowing mixture comes out as a two-phase aqueous-organic solution. The aqueous phase was separated and discarded, and the solvent from the organic phase was evaporated under reduced pressure. The crude product was dissolved in ethyl acetate and extracted into 1 M HCl. Neutralization with $NaHCO_3$ and re-extraction into ethyl acetate provided the imidazole compound of formula 6 after drying with $Na_2SO_4$ and evaporation of the solvent.

In one embodiment, the reaction of compound of formula 5 with the reagent occurs in presence of a base and a solvent, wherein, the reagent is selected from the group consisting of ammonium acetate, ammonium formate, ammonium sulfamate, ammonium phosphate, ammonium citrate, ammonium carbamate, ammonia, and mixtures thereof.

The continuous manufacturing platform produces on-demand medicinally privileged formula 6 with good yields (Table 5) and results are comparable with the previously reported microreactor work (*ACS Sustainable Chemistry and Engineering*, 3, 3445-3453 (2015)).

TABLE 5

Reaction optimization for the imidazole 6 formation.

| Entry | Flow rate (ml/min) 5 solution | Flow rate (ml/min) $NH_4OAc$ | Stoichiometric ration (Formula 5:$NH_4OAc$) | Retention time (min) | % Yield of 6 |
|---|---|---|---|---|---|
| 1 | 1.5 | 2.5 | 1:57.3 | 4 | 76 |
| 2 | 2.5 | 1.5 | 1:20.64 | 4 | 75 |
| 3 | 3.5 | 0.5 | 1:4.9 | 4 | 73 |
| 4 | 3.75 | 0.25 | 1:2.29 | 4 | 55 |

Reaction condition: 5 (0.25M) and the N-boc-L-proline (0.26M) in MeCN;
triethylamine (1.2M);
Yield are based on isolated yield.

Step e) In deprotection step, a solution of reactants of formula 6, and aqueous HCl in a protic solvent are pumped into the continuous micro-electro-flow reactor; maintaining the reaction mixture in reactor for about 1-5 minutes at a temperature of about 20-40° C. and at a pressure of about 1-10 bar followed by the process known in the prior art for extraction and isolation of a compound of formula 7.

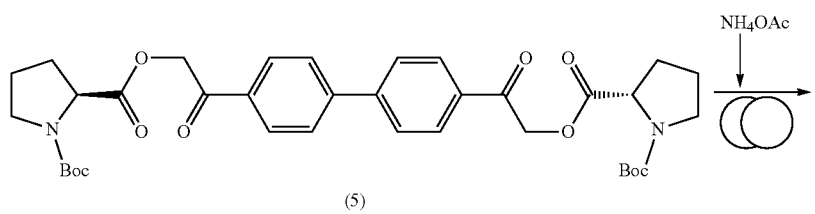

(5)

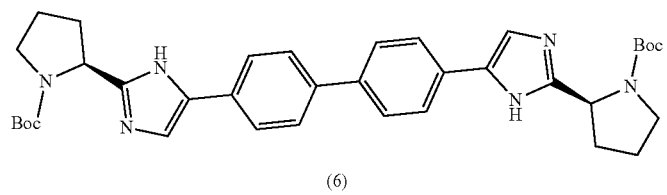

(6)

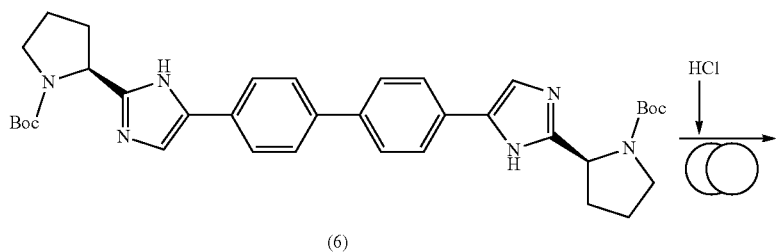

(6)

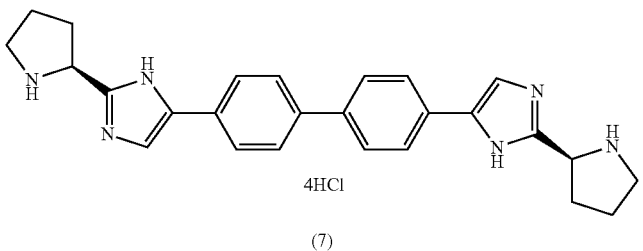

(7)

In one embodiment, the reaction of compound of formula 6 is carried out using a deprotecting agent in the presence of solvent, wherein, the deprotecting agent is selected from the group consisting of HCl, H$_2$SO$_4$, HNO$_3$, trimethylsilyl iodide, and mixtures thereof and the solvent is selected from the group consisting of alcohol solvents, ester solvents, and mixtures thereof.

Table 6, shows optimization reaction conditions to get BOC-deprotection (7) with excellent yields (76%, Table 6, entry 1) in 3 minutes of reaction time, while macro-reactor needs 5 hours (Bioorganic Medicinal Chemistry and Letter, 22, 4864-4868, (2012)).

TABLE 6

Reaction optimization for the BOC-Deprotection formation.

| | Flow rate (ml/min) | | Stoichiometric ratio | Retention | % |
|---|---|---|---|---|---|
| Entry | Formula 6 | aq. HCl | (Fomula 6:HCl) | time (min.) | Yield of 7 |
| 1 | 1.0 | 0.35 | 1:21 | 7.4 | 99 |
| 2 | 2.0 | 0.35 | 1:10.5 | 4.25 | 99 |
| 3 | 3.0 | 0.35 | 1:7 | 3 | 99 |
| 4 | 4.0 | 0.35 | 1:5.25 | 2.3 | 71 |

Stock solution 6: 0.1M in MeCN; 6N HCl.
Yields are based on LC-MS.

Step f) In final step, pumping a solution of reactants of formula 7, Moc-L-valine, base such as DIPEA or TEA, HOBt, and EDC.HCl and coupling agent; such as 1,1'-carbonyldiimidazole, bis(2-oxo-3-oxazolidinyl)phosphinic chloride, 1-hydroxy-7-azabenzotriazole, 1-hydroxybenzotriazole hydrate, 3-hydroxyl-2, 3-benzotriazin-4(3H)-one, 1-(3-dimethyaminopropyl)-3-ethylcarbodiimide hydrochloride, 4-nitrophenol, pentafluorophenol, 2-hydroxypyridine, N-hydroxysuccinimide, N-hydroxyphthalamide, 2-mercaptobenzoxazole, trimethylacetyl chloride, isobutylchloroformate, chlorodimethoxytriazole, oxalyl chloride, 2-hydroxypyridine-N-oxide, 5-nitro-2-hydroxypyridine, Boc-L-valine anhydride, and mixtures thereof; in a polar aprotic solvent (examples of solvents include isopropyl acetate, acetone, NMP, dichloromethane, 2-methyltetrahydrofuran, ethyl acetate, and acetonitrile) into the continuous micro-electro-flow reactor; maintaining the reaction mixture in reactor for about 20-100 minutes at a temperature of about 20-40° C. and at a pressure of about 1-10 bar followed by the extraction and removing organic solvents to obtain daclatasvir of Formula I.

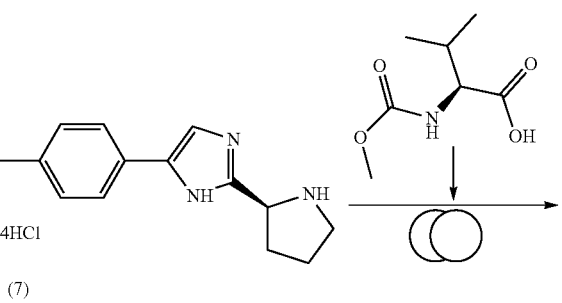

(7)

-continued

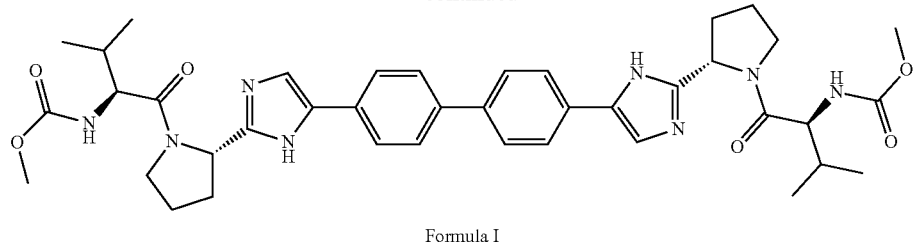

Formula I

Individual conditions will vary depending on the nature of the coupling reagent, retention time, temperature, pressure and will be known to those of ordinary skill in the art (Table 7).

TABLE 7

Reaction optimization for the daclatasvir (I) synthesis.

| Entry | Flow rate (µl/min) Formula 7 + DIPEA | Moc-L-Valine + EDC · HCl + HOBt | Stoichiometric ratio (Formula 7:MOC-L-Val) | Retention time (min.) | Formula I Yield (%) |
|---|---|---|---|---|---|
| 1[a] | 100 | 100 | 1:3.3 | 50 | ~94 |
| 2[b] | 100 | 100 | 1:3.3 | 50 | ~2 |

Formula 7: 0.017M in DMF, DIPEA 5.5 equiv.;
MOC-L-Valine (0.057M), EDC · HCl (2.5 equiv.), HOBt (2.5) in (a) DMF and (b) ethanol solvent, yields are based on isolated yield.

In an embodiment, the present invention provides that the continuous flow process system is employed for bulk scale preparation of daclatasvir (formula I).

EXAMPLES

Following examples are given by way of illustration and therefore should not be construed to limit the scope of the invention Material and Method Used in Experiments Most of the reagents and chemicals were bought from Spectrochem, AVRA and Sigma-Aldrich, which were used as such without any further purification. Common organic chemicals and salts were purchased from AVRA chemicals, India.

Deionized water (18.2 mS conductivity) was used in all experiments. All work-up and purification procedures were carried out with reagent-grade solvents. Analytical thin-layer chromatography (TLC) was performed using analytical chromatography silica gel 60 F254 pre-coated plates (0.25 mm). The developed chromatogram was analysed by UV lamp (254 nm).

PTFE (id=100-1000 µm) tubing, T-junction and back-pressure controller (BPR) were procured from Upchurch IDEX HEALTH & SCIENCE. Pump purchased from KNAUER. SS318 capillary bought from the spectrum market, Mumbai, India. Heating reactor bought from the Thales Nano Nanotechnology, Inc.

Measurement Method

High-resolution mass spectra (HRMS) were obtained from a JMS-T100TD instrument (DART) and Thermo Fisher Scientific Exactive (APCI).

Nuclear magnetic resonance (NMR) spectra were recorded on a Bruker 600, 500, 400 or 300 MHz instrument in $CDCl_3$ or $DMSO-d_6$ solvent. Chemical shifts for $^1H$ NMR are expressed in parts per million (ppm) relative to tetramethylsilane (δ 0.00 ppm). Chemical shifts for $^{13}C$ NMR are expressed in ppm relative to $CDCl_3$ (δ 77.0 ppm). Data are reported as follows: chemical shift, multiplicity (s=singlet, d=doublet, dd=doublet of doublets, t=triplet, q=quartet, quin=quintet, sext=sextet, m=multiplet), coupling constant (Hz), and integration. GC/MS analysis was conducted on Shimadzu technology GCMS-QP2010 instrument equipped with a HP-5 column (30 m×0.25 mm, Hewlett-Packard) and inbuilt MS 5975C VL MSD system with triple axis detector. ATR analysis was conducted on Portable FTIR spectrometer Bruker ALPHA.

List of Abbreviations

Figure 1:
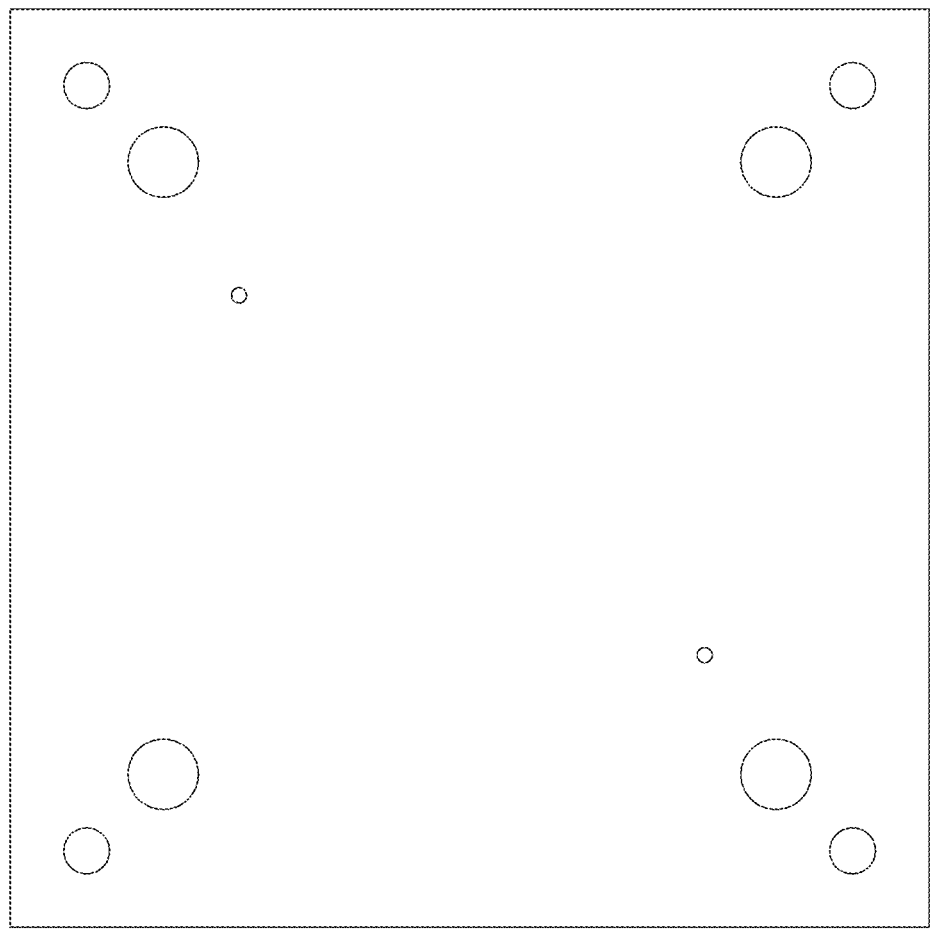
FIG. 1 illustration of the micro electro-flow outer body design. We have fabricated micro electro-flow with a stainless-steel body, (60 mm length×60 mm width×10 mm thickness).
Figure 2:
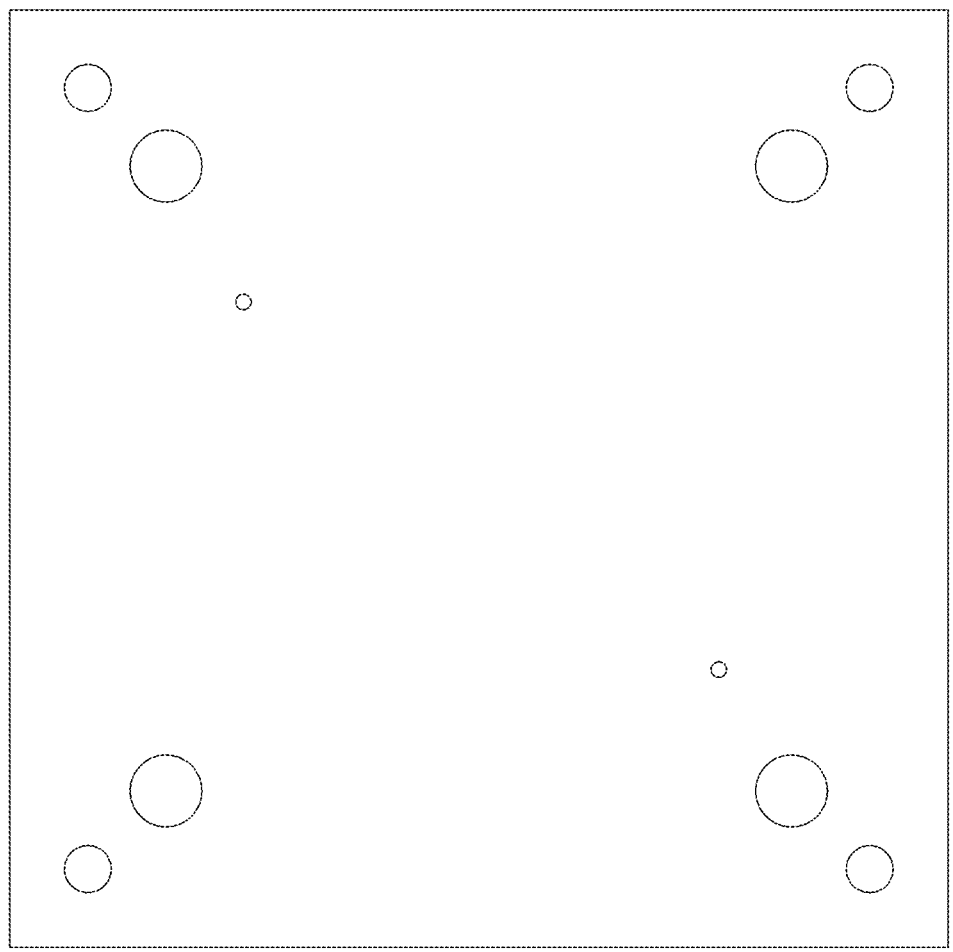
FIG. 2: illustration of micro electro-flow the second layer fabricated with teflon (60 mm length×60 mm width×1 mm thickness) layer made with laser cutter for protecting the stainless steel from the corrosive acid base and insulator for the current flow.
Figure 3:
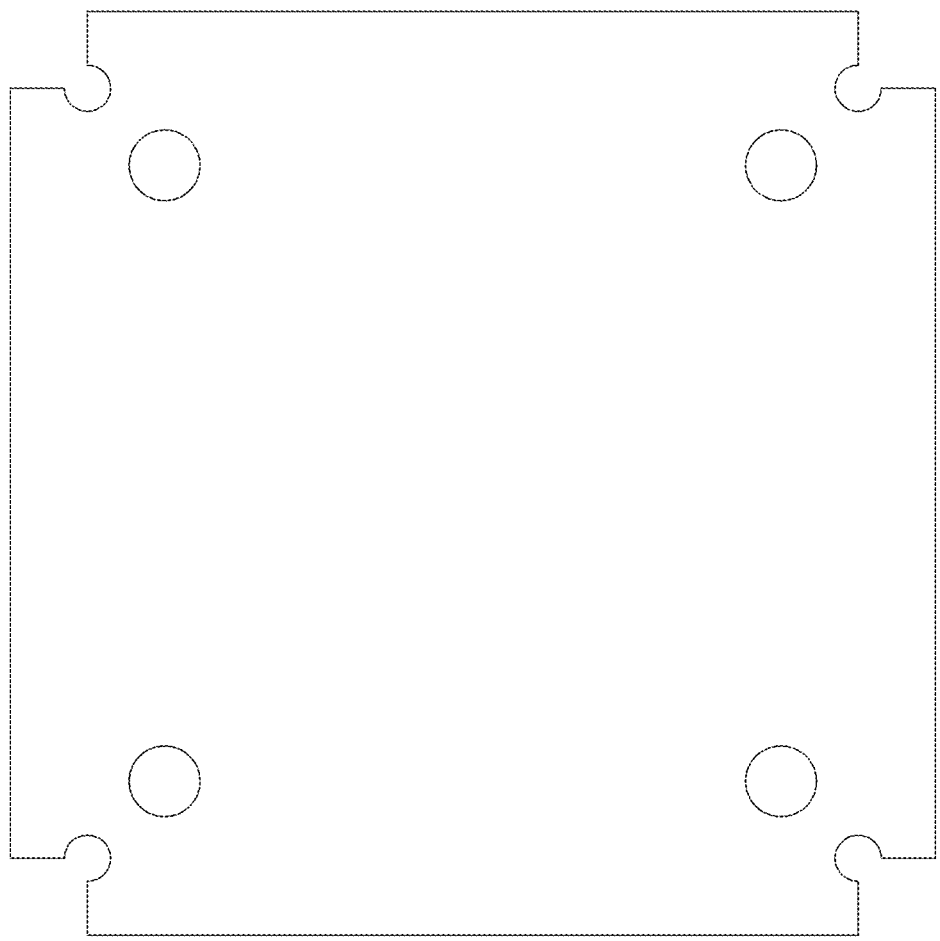
FIG. 3 Illustration of graphite cathode customized with our reactor size (60 mm length×60 mm width×2 mm thickness).
Figure 4:
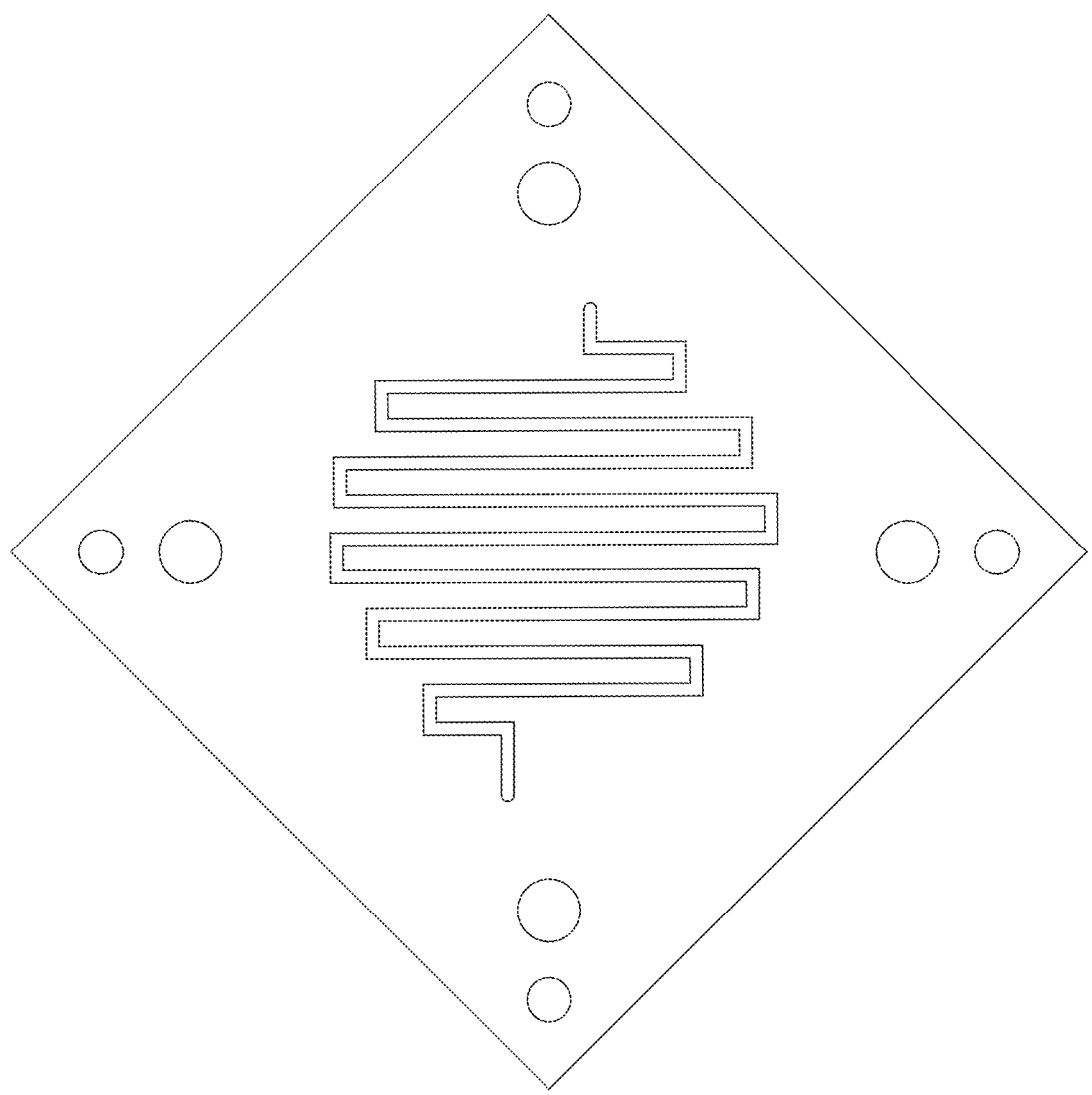
FIG. 4 illustration of the solution pathway third layer comprising of a laser cutted teflon plastic (60 mm×60 mm×1 mm thickness) zig-zag groove with rectangular shape (2 mm×80.0 mm).
Figure 5:
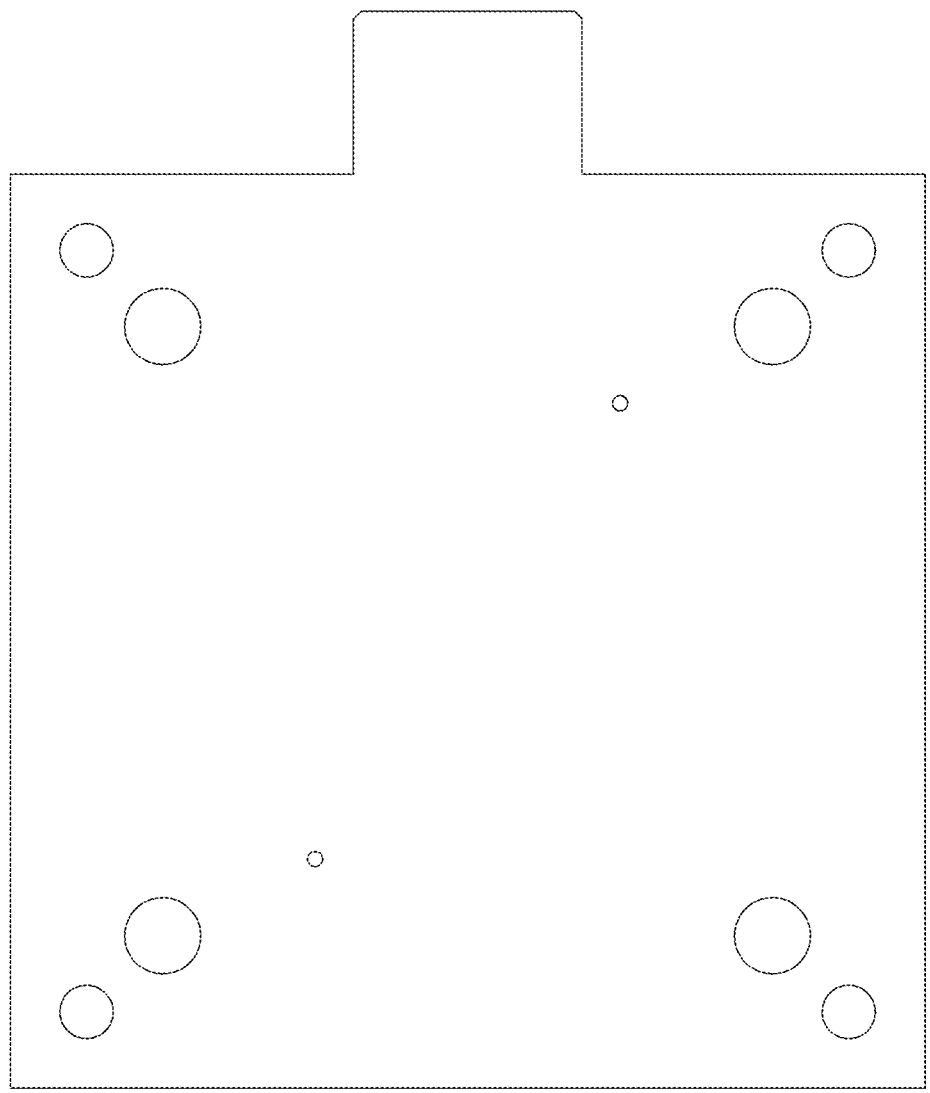
FIG. 5 Illustration of copper anode customized with our reactor size (60 mm length×60 mm width×2 mm thickness).
Figure 6:
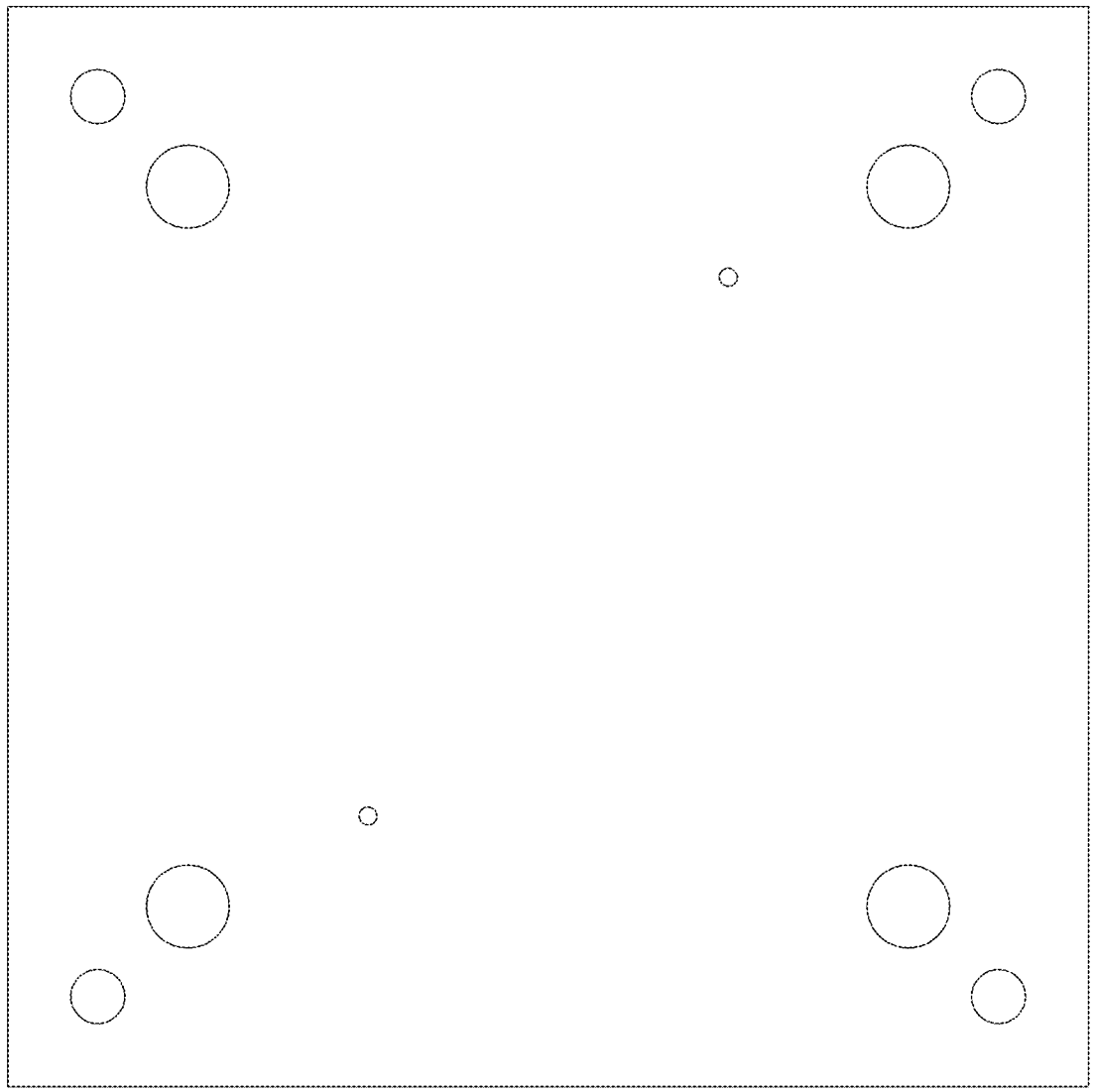
Figure 7:
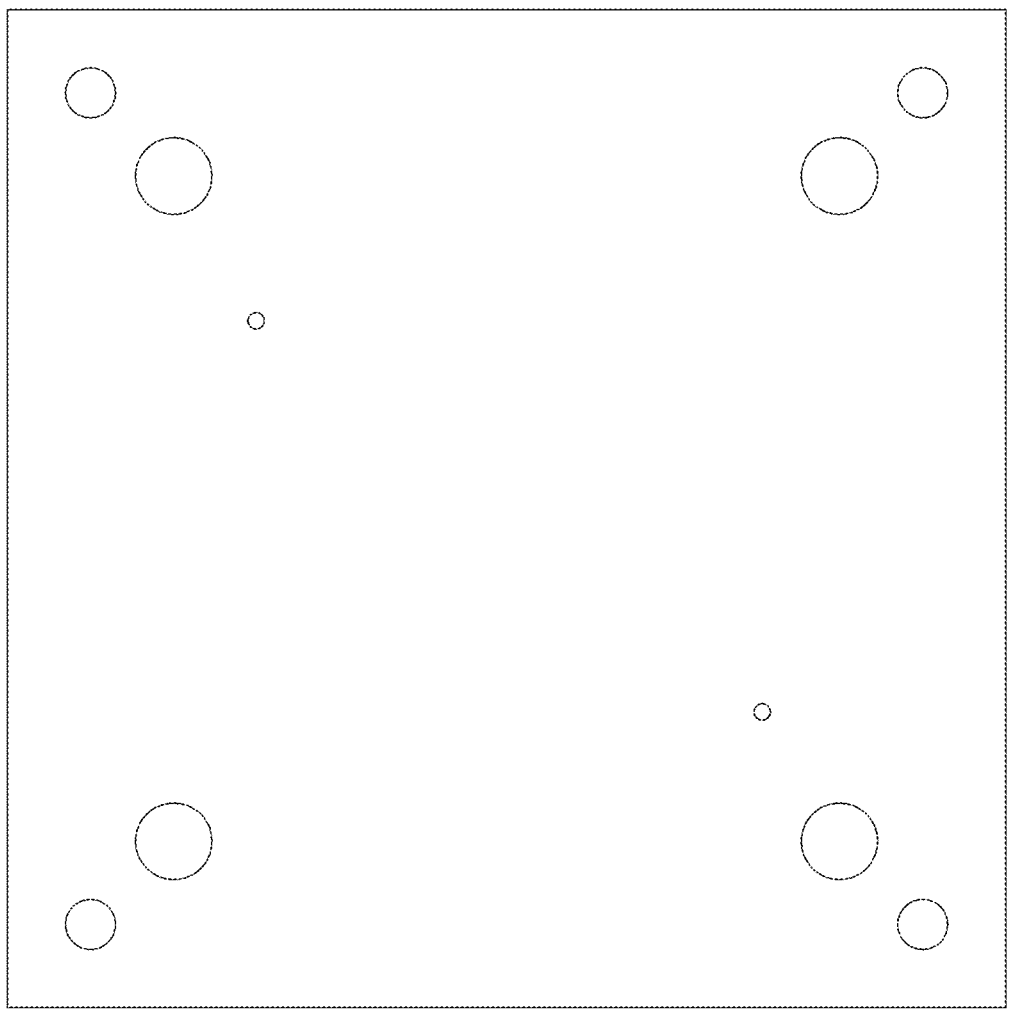

BPR=Back pressure regulator
DCM=Dichloromethane
ETFE=Ethylene tetrafluoroethylene
GC=Gas chromatography
HPLC=High pressure Liquid chromatography
HRMS=High resolution mass spectroscopy
ID=Inner Diameter
IR=Infra-red
MSD=Multiple Spark Discharge
NMR=Nuclear Magnetic resonance
OD=Outer Diameter
PE=Polyethylene
PFA=Perfluoroalkoxy alkane
PTFE=Polytetrafluoroethylene
SS=Stainless Steel
TLC=Thin layer chromatography
UV=Ultra-Violet General Procedure for the Designing of Micro-Electrolysis Flow Reactor (µ-EFR):

1. The first layer of Micro electro-flow reactor was fabricated with a stainless-steel body FIG. 1 (60 mm length× 60 mm width×10 mm thickness).
2. The second layer was fabricated with teflon layer (60 mm length×60 mm width×1 mm thickness) grooved with laser cutter for protecting the stainless steel from the corrosive acid base and insulator for the current flow.
3. The third layer was fabricated with graphite cathode customized with our reactor size (60 mm length×60 mm width×2 mm thickness).
4. Fourth layer was fabricated with teflon plastic (60 mm×60 mm×1 mm thickness) zig-zag groove with rectangular shape (2 mm×80.0 mm).
5. Fifth layer was fabricated with copper plate customized with our reactor size (60 mm length×60 mm width×2 mm thickness).
6. Finally, the 4-corners of each two Teflon films were drilled to make a hole (1 mm diameter). Thereafter, both the electrodes were merged by teflon zig-zag channel sheets with identical dimension to fit groove channels and coupled to each other by inserting metal pins through the holes at the film corners.
7. Ni@Cu anode preparation: Ni nanoparticles were patterned over copper plate made by electrodeposition method (*Surface and Coatings Technology*, 126, 48-63 (2000). In this method, copper plate was cleaned by 2N acetic acid, followed by deionized water to remove oxidized layer and dried by $N_2$ flow. Then, the copper plate was sandwiched between the above designed reactor and connected with pump. Copper plate was connected with negative charge and graphite plate connected with positive charge. 0.125 wt. % Ni.acetate.$H_2O$ in water solution was passed through the microreactor channel with flow rate of 0.100 mL $min^{-1}$ at 2V for 2 h, which typically led to the generation of an ash colored patterning, and then washed with water thoroughly to remove any unreacted salt and nanoparticle (FIG. 8).
8: Pt@Ni@Cu anode preparation: modified phosphates bath-based method has been used for deposition of Pt over the Ni nano-particle. In this method, stock electrolytic solution contains mixture of Pt(IV) chlorides 150 mg, diammonium hydrogen phosphate $(NH_4)_2HPO_4$ 80 mg, disodium hydrogen phosphate $(Na)_2HPO_4$ 200 mg, Ammonium chloride 50 mg, and water 10 mL, was pumped with fix flow rate of 0.100 mL $min^{-1}$ for 2 h at 70° C. under current density of 0.3 $A/dm^2$, which typically led to the generation of a black colored patterning, and then washed with water thoroughly to remove any unreacted salt and nanoparticle. Xanthostemon chrysanthus flower shape pattern morphology was confirmed by SEM/EDX (FIG. 9).

General Procedure for the Synthesis of Core Biphenyl Moiety of Formula (3A-3H):
1. A solution containing reactants, catalysts, ligand and solvent under stoichiometric molar ratios of [1a-1i/ $NiCl_2$.glyme/LiCl/DMA MeOH/$H_2O$] was taken in syringe and connected with μ-EFR as described in FIG. 12.
2. The reactant mixture containing the above solution was introduced into a μ-EFR (Height=800-1000 μm, length=8-10 cm, width=1-2 mm, reactor volume 200-400 μl) for the synthesis of symmetrical biaryls during 4-40 min. of residence time and 4-10 mA current.
3. In next step, reaction mixture was basified and solvent exchange (from hydrophilic solvent DMA to low boiling hydrophobic solvent such as DCM, toluene, and diethyl ether) was done by introducing basic water and low boiling solvent through extracting funnel.
4. The low boiling solvent was removed from organic extract under reduced pressure to obtain the crude compound.
5. The crude compound was purified by column chromatography (hexane/ethyl acetate) to give the corresponding products (3a-3h).

Example 1

Synthesis of Biphenyl (3a)

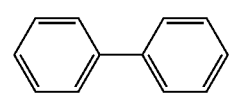

3a

A μ-EFR (Graphite cathode and Pt@Ni@Cu anode, height=1000 μm, length=10 cm, width=2 mm, reactor volume 200 μl, total electrode contacts surface area 400 $mm^2$) was assembled and joined to the other components of the continuous flow system to ensure efficient mixing and high surface to volume ratio. The stock solution containing a mixture of bromobenzene (1a) (0.025 g, 0.015 mmol,) and $NiCl_2$.glyme (0.003 g, 10 mol %), 2,2'-bipyridine (1.9 mg, 10 mol %), LiCl (24 mg, 0.06 mmol) in 1 mL of DMA was passed through the pre-designed μ-EFR, keeping 4 min. residence time and 4 mA constant current. Finally, outflowing product mixture was quenched and solvent exchange was done from DMA: water to low boiling solvent diethyl ether by adding aq. NaCl solution. Extracted waste water layer was further extracted with diethyl ether and analyzed by LC-MS, which showed no traces of product and was again confirmed by absence of the corresponding peaks in crude NMR analysis ($^1H$ and $^{13}C$ NMR spectra). The organic extract (diethyl ether layer) was concentrated and the resulting residue was purified by silica gel column chromatography (100% petroleum ether) to provide an off-white solid (3a) (11.31 mg, 98%), melting point: 69° C. The spectral data matched with values reported in the literature (Organic Lett. 15, 2664-2667 (2013).

$^1H$ NMR (500 MHz, $CDCl_3$) δ 7.70-7.65 (m, 4H), 7.54-7.49 (m, 4H), 7.45-7.39 (m, 2H).

$^{13}C$ NMR (126 MHz, $CDCL_3$) δ 141.20, 128.72, 127.21, 127.12.

IR ($v_{max}$): 3046, 1479, 1429, 739, 698 $cm^{-1}$;

MS (EI): found: 154 ($M^+$)

Example 2

Synthesis of 4,4'-dimethyl-1,1'-biphenyl (3b)

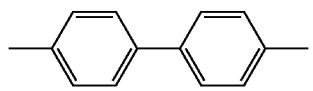

3b

Compound of formula (3b) was synthesised following the procedure described above under Example 1 and general procedure involving corresponding reactants of formula (1b). The crude material was purified by silica gel column chromatography (100% PE) to provide a white solid (12.43 mg, 91%); melting point: 118° C.; The spectra data matched with values reported in the literature (*Angew. Chem. Int. Ed.* 53, 3475-3479 (2014).

$^1$H NMR (400 MHz, CDCl$_3$) δ 7.47 (d, J=7.9, 4H), 7.22 (d, J=7.8, 4H), 2.38 (s, 6H).

$^{13}$C NMR (101 MHz, CDCL$_3$) δ 138.26, 136.66, 129.41, 126.78, 21.06.

IR ($v_{max}$): 3020, 2924, 2856, 1495, 1106, 1026, 801, 706 cm$^{-1}$;

MS (EI): found: 182 (M$^+$).

Example 3

Synthesis of 3, 3'-dimethyl-1,1'-biphenyl (3c)

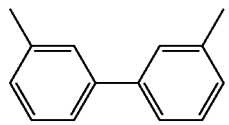

3c

Compound of formula (3c) was synthesised following the procedure described above under Example 1 and general procedure involving corresponding reactants of formula (1c). The crude material was purified by silica gel column chromatography (100% PE) to provide a white solid (10.37 mg, 76%); Melting point: 150° C.; The spectra data matched with values reported in the literature (*J. Org. Chem.* 79, 2733-2738 (2014).

$^1$H NMR (400 MHz, CDCl$_3$) δ $^1$H NMR (400 MHz, CDCl$_3$) δ 7.40-7.28 (m, 4H), 7.23 (t, J=7.5 Hz, 2H), 7.06 (t, J=13.2 Hz, 2H), 2.33 (s, 6H). $^{13}$C NMR (101 MHz, CDCL$_3$) δ 141.33, 138.21, 128.57, 127.95, 127.88, 124.26, 21.52.

IR ($v_{max}$): 3021, 2924, 1600, 1472, 1216, 758, 708, 66. cm$^{-1}$;

MS (EI): found: 182 (M$^+$).

Example 4

Synthesis of 1,1'-binaphthalene (3d)

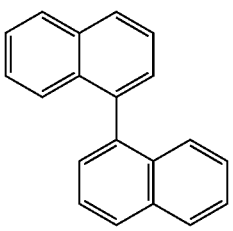

3d

Compound of formula (3d) was synthesised following the procedure described above under Example 1 and general procedure involving corresponding reactants of formula (1d). The crude material was purified by silica gel column chromatography (100% PE) to provide a white solid (14.10 mg, 74%); Melting point: 159° C. The spectra data matched with values reported in the literature (*Angew. Chem. Int. Ed.* 55, 3620-3624 (2016).

$^1$H NMR (400 MHz, CDCl$_3$) 7.91 (dd, J=8.2, 3.3 Hz, 2H), 7.66-7.55 (m, 1H), 7.54-7.41 (m, 2H), 7.38 (d, J=7.8 Hz, 1H), 7.25 (ddd, J=8.3, 6.7, 1.2 Hz, 1H). $^{13}$C NMR (101 MHz, CDCL$_3$) δ 138.42, 133.49, 132.82, 128.12, 127.86, 127.80, 126.53, 125.94, 125.77, 125.35.

IR ($v_{max}$): 3023, 1215, 740, 670 cm$^{-1}$;

MS (EI): found: 254.11 (M$^+$).

Example 5

Synthesis 2, 2'-binaphthalene (3e)

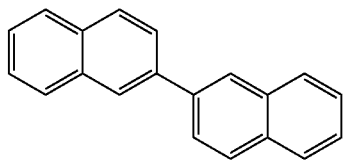

3e

Compound of formula (3e) was synthesised following the procedure described above under Example 1 and general procedure involving corresponding reactants of formula (1e). The crude material was purified by silica gel column chromatography 100% PE) to provide a white solid (13.92 mg, 73%); Melting point: 184° C.; The spectra data matched with values reported in the literature (*Angew. Chem. Int. Ed.* 55, 3620-3624 (2016).

$^1$H NMR (400 MHz, CDCl$_3$) δ 7.96-7.87 (d, J=4.3 Hz, 4H), 7.66-7.58 (t, J=7.4 Hz, 2H), 7.54-7.44 (m, 4H), 7.39 (d, J=8.4 Hz, 2H), 7.31-7.23 (m, 2H).

δ $^{13}$C NMR (126 MHz, CDCl$_3$) δ 138.43, 133.49, 132.82, 128.12, 127.86, 127.80, 126.53, 125.95, 125.78, 125.35.

IR ($v_{max}$): 3023, 1215, 741, 670 cm$^{-1}$;

MS (EI): found: 254.11 (M$^+$)

Example 6

Synthesis of 1,1':4',1":4",1'''-quaterphenyl (3f)

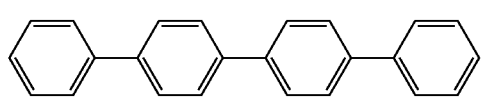

3f

Compound of formula (3f) was synthesised following the procedure described above under Example 1 and general procedure involving corresponding reactants of formula (1f). The crude material was purified by silica gel column chromatography (100% PE) to provide a white solid (16.56 mg, 72%); Melting point: 298° C. The spectra data matched with values reported in the literature (*J. Am. Chem. Soc.* 139, 4769-4779 (2017).

$^1$H NMR (500 MHz, CDCl$_3$) δ 7.63-7.55 (m, 8H), 7.50-7.42 (m, 8H), 7.38 (t, J=7.3 Hz, 2H).

$^{13}$C NMR (126 MHz, CDCl$_3$) δ 140.11, 139.97, 131.90, 128.86, 128.87, 127.68, 126.98, 121.57.

IR ($v_{max}$): 3734, 3422, 3026, 2928, 1958, 1897, 1727, 1659, 1592, 1476, 1391, 1272, 1211, 1076, 1004, 828, 756, 693 cm$^{-1}$;

MS (EI): found: 306.14 (M$^+$).

Example 7

Synthesis of 1,1'-([1,1'-biphenyl]-4,4'-diyl) diethanone (3g)

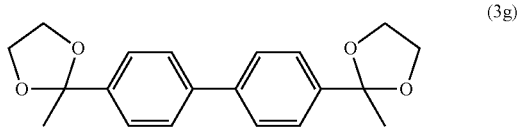 [SMILES: CC1(c2ccc(-c3ccc(C4(C)OCCO4)cc3)cc2)OCCO1]

(3g)

Compound of formula (3g) was synthesised following the procedure described above under Example 1 and general procedure involving corresponding reactants of formula (1g). The crude material was purified by silica gel column chromatography (hexane/ethyl acetate; 95:05) to provide a white solid (16.91 mg, 79%); Melting point: 148° C.; The spectra data matched with values reported in the literature (Bioorg. Med. Chem. Lett., 20(15), 4544-4549; 2010).

$^1$H NMR (400 MHz, CDCl$_3$) δ 7.50-7.42 (m, 2H), 7.39-7.32 (m, 2H), 4.08-3.98 (m, 2H), 3.81-3.70 (m, 2H), 1.63 (s, 3H).

$^{13}$C NMR (75 MHz, CDCl$_3$) δ 142.44, 131.28, 127.13, 121.83, 108.41, 64.45, 27.49.

IR ($v_{max}$): 3390, 2980, 2888, 1479, 1383, 1245, 1197, 1082, 1031, 876, 825 cm$^{-1}$;

MS (EI): found: 326.15 (M$^+$).

Example 8

Synthesis of 1,1'-([1,1'-biphenyl]-4,4'-diyl) diethanone (3h)

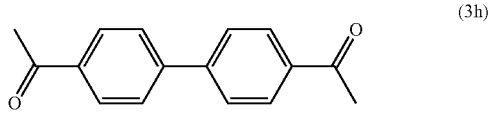 [SMILES: CC(=O)c1ccc(-c2ccc(C(C)=O)cc2)cc1]

(3h)

A μ-EFR (Graphite cathode and Ni@Cu anode, height=1000 μm, length=10 cm, width=2 mm, reactor volume 200 μl total electrode contacts surface area 400 mm$^2$) was assembled and joined to the other components of the continuous flow system to ensure efficient mixing. The stock solution was prepared in a 10 mL volumetric flask under anhydrous condition before injecting into μ-EFR with Ni@Cu anode through a syringe pump. The stock solution containing a mixture of 1 h (0.025 g, 0.015 mmol,) and NiCl$_2$.glyme (0.003 g, 10 mol %), 2,2'-bipyridine (1.9 mg, 10 mol %), LiCl (24 mg, 0.06 mmol) and phase transfer catalyst TBAI (25 mol %) in 1 mL of DMA was passed through the pre-designed μ-EFR, keeping 200 min. residence time and 4 mA constant current. Finally, out-flowing product mixture was quenched and solvent exchange was done from DMA: water to low boiling solvent diethyl ether by adding aq. NaCl solution. Extracted waste water layer was further extracted with diethyl ether and analyzed by LC-MS, which showed no traces of product and was again confirmed by absence of the corresponding peaks in crude NMR analysis ($^1$H and $^{13}$C NMR spectra). The crude material was purified by silica gel column chromatography (hexane/ethyl acetate; 95:05) to provide a white solid (16.15 mg, 89%); Melting point: 144° C.;

The spectra data well matched with values reported in the literature Org. Process Res. Dev. 2018, 22, 1614-1621.

1H NMR (400 MHz, CDCl3) δ 1H NMR (500 MHz, CDCl3) δ 8.12-7.97 (m, 2H), 7.79-7.64 (m, 2H), 2.65 (s, 3H).

13C NMR (101 MHz, CDCl3) δ 197.61, 144.33, 136.58, 129.03, 127.46, 26.73.

IR (v max): 1677, 1597, 1358, 1267, 954, 816 cm-1;

MS (EI): found: 238.10 (M+).

Example 9

Synthesis of 1,1'-([1,1'-biphenyl]-4,4'-diyl) bis(2-bromoethanone) (4)

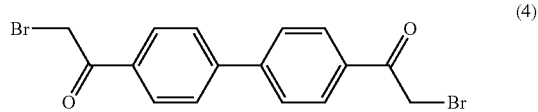 [SMILES: O=C(CBr)c1ccc(-c2ccc(C(=O)CBr)cc2)cc1]

(4)

A solution of compound of formula 3h in dichloromethane (DCM) (1.0 M) and a solution of Br$_2$ in DCM (2.0 M) were introduced into the capillary microreactor with a T-mixer using two separate syringe pumps. The flow rate of the formula 3h solution was kept at same rate as of Br$_2$, in accordance with the stoichiometry of reagent and substrates. However, right after mixing of the two solutions (formula 3h and Br$_2$), a tube-plugging problem was encountered, presumably due to formation of a partial soluble formula 4 which precipitated in DCM. To solve the clogging problem, the solution was further diluted (100 times) with DCM and resulting reaction mixture then smoothly passed through perfluoroalkoxy (PFA) tubing (inner diameter (id)=1000 μm, length=20 m, volume=15.7 mL) for the reaction to occur. A residence time (RT) of 75 min was found to be enough for the bromination of the formula 3h to form the compound of formula 4 (Table 3, entry 2). The solvent was removed under vacuum and the residue was further triturated by n-pentane to give the compound of formula 4 with 93% yield. Melting point: 202° C.; The spectra data matched with values reported in the literature (Medicinal Chemistry Research, 24, 2632-2644, 2015).

$^1$H NMR (400 MHz, CDCl$_3$) δ 7.95-7.85 (m, 4H), 7.60-7.50 (m, 4H), 4.26 (s, 4H);

$^{13}$C NMR (100 MHz, CDCl$_3$) 191.0, 145.1, 133.8, 129.9, 127.9, 30.8

IR ($v_{max}$): 3002, 2946, 1687, 1592, 1548, 1389, 1278, 1194, 1137, 984, 805, 699 cm$^{-1}$;

MS (EI): found: 393.92 (M$^+$).

Example 10

Synthesis of (2S,2'S)—O'2, O2-([1,1'-biphenyl]-4,4'-diylbis(2-oxoethane-2,1-diyl)) 1-di-tert-butyl bis(pyrrolidine-1,2-dicarboxylate) (5)

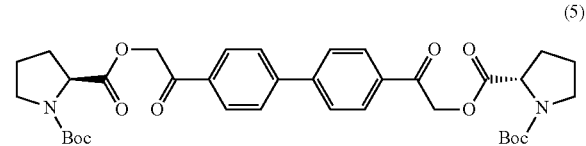

(5)

The suspension of 4 (0.25 M) and the N-boc-L-proline (0.5 M) in MeCN (Sol" 2 & N-boc-L-proline Feed A) and triethylamine (1.2 M) in MeCN (Sol" TEA Feed B), and were introduced into the flow reactor from an injection loop. Feed A and feed B were mixed in a Y-shaped mixer and the combined mixture was passed through perfluoroalkoxy (PFA) tubing (inner diameter (id)=1000 μm, length=12.8 m, volume=10 mL) at 60° C. (2.5 min). The flow rates for feed A and feed B are shown in Table 4. The organic layer containing crude product 5 was taken further for the next reaction without further purification.

Spectral data: $^1$H NMR (300 MHz, CDCl$_3$) δ 8.01 (dd, J=7.8, 4.3 Hz, 4H), 7.74 (d, J=8.1 Hz, 4H), 5.61 (d, J=16.5 Hz, 1H), 5.51-5.32 (m, 2H), 5.25 (d, J=16.5 Hz, 1H), 4.51 (dd, J=8.2, 3.8 Hz, 1H), 4.43 (t, J=6.2 Hz, 1H), 3.67-3.35 (m, 4H), 2.32 (td, J=14.2, 5.8 Hz, 4H), 2.18-1.86 (m, 4H), 1.46 (d, J=5.9 Hz, 18H).

$^{13}$C NMR (126 MHz, CDCl$_3$) δ 191.44, 172.56, 154.15, 144.85, 133.65, 128.43, 127.72, 79.90, 66.00, 58.85, 46.51, 30.55, 28.37, 23.92.

IR ($v_{max}$): 2976, 1758, 1698, 1401, 1238, 1165, 967 cm$^{-1}$; MS (EI): found: 664.30 (M$^+$).

Example 11

Synthesis of (2S,2'S)-di-tert-butyl 2,2'-(5,5'-([1,1'-biphenyl]-4,4'-diyl)bis(1H-imidazole-5,2-diyl))bis(pyrrolidine-1-carboxylate) (6)

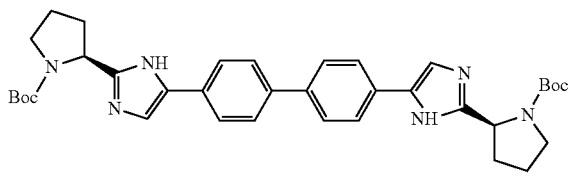

(6)

A solution of compound of formula 5 in MeCN (Sol" 2 Feed A; 0.25 M) and ammonium acetate in water (feed B; 8.6 M) were mixed in a Y-shaped mixer and the combined mixture was passed through stainless steel tubing at 160° C. The flow rates for feed A and feed B are shown in Table 5. The processed solution was cooled in a heat exchanger and finally left the system through a back pressure regulator (250 psi). The processed mixture left the flow reactor as a two phase water/MeCN solution. The aqueous phase was removed and discarded, and the solvent from the organic phase was removed under reduced pressure. The crude product was dissolved in ethyl acetate and extracted into 1 M HCl. Neutralization with NaHCO$_3$ and re-extraction into ethyl acetate provided the imidazole derivative after drying with Na$_2$SO$_4$ and evaporation of the solvent.

Spectral data: $^1$H NMR (400 MHz, DMSO-d$_6$) δ 13.00-11.00 (s, 2H). 7.78 (d, J=8.0 Hz, 4H), 7.65 (d, J=8.2 Hz, 4H), 7.38 (s, 2H), 4.84 (d, J=4.8 Hz, 2H), 3.54 (m, 2H), 3.49-3.28 (m, 2H), 3.11 (m, 2H), 2.20-1.87 (m, 6H), 1.60-1.33 (s, 8H), 1.28 (s, 10H)

$^{13}$C NMR (100 MHz, DMSO-d$_6$) δ 154.1, 150.96, 137.5, 126.6, 125.0, 78.9, 78.5, 55.6, 55.0, 47.0, 46.7, 33.7, 32.2, 28.5, 28.2, 24.2, 23.5.

IR (KBr, cm$^{-1}$) 2974, 1676, 1403, 1164, 1125 cm$^{-1}$; MS (EI): found: 624.34 (M$^+$).

Example 12

Synthesis of 4,4'-bis(2-((S)-pyrrolidin-2-yl)-1H-imidazol-5-yl)-1,1'-biphenyl tetrahydrochloride (7)

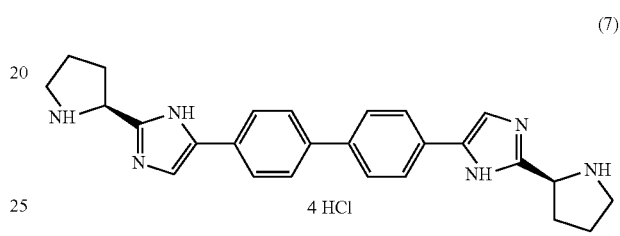

(7)

A solution of compound of formula 6 in MeCN (0.1 M) and an aq. solution of HCl (6N) were introduced into the capillary microreactor with a T-mixer using two separate syringe pumps at a flow rate ratio of 1:7 to maintain the stoichiometry and then passed through a PTFE tubing (id=1000 μm, l=12.8 m) towards deprotection of BOC during 3 min of residence time and 60° C. temperature (Table 6, entry 3). Filtration of the slurry afforded a solid which was washed successively with 30 mL of 90% methanol/water (V/V) and 2×20 mL of methanol. The wet cake was dried in vacuum at 50° C. to give 99% of LC-MS yield of compound of formula 7.

Spectral data: $^1$H NMR (500 MHz, DMSO) δ 10.46 (s, 1H), 10.03 (s, 1H), 8.23 (s, 1H), 8.07 (d, J=8.4 Hz, 2H), 7.93 (d, J=8.5 Hz, 2H), 5.09 (t, J=7.9 Hz, 1H), 3.60-3.44 (m, 1H), 3.41-3.33 (m, 1H), 2.30-2.19 (m, 1H), 2.02 (ddd, J=17.1, 8.5, 4.3 Hz, 1H). $^{13}$C NMR (101 MHz, DMSO) δ; 141.89 (s), 139.35 (s), 133.48 (s), 127.27 (s), 126.72 (s), 126.02 (s), 116.51 (s), 52.20 (s), 45.57 (s), 29.49 (s), 24.15 (s).

IR ($v_{max}$): 3372, 2885, 2711, 1633, 821 cm$^{-1}$; MS (EI): found: 568.14 (M$^+$).

Example 13

Synthesis of Daclatasvir Dihydrochloride of Formula I

Formula I

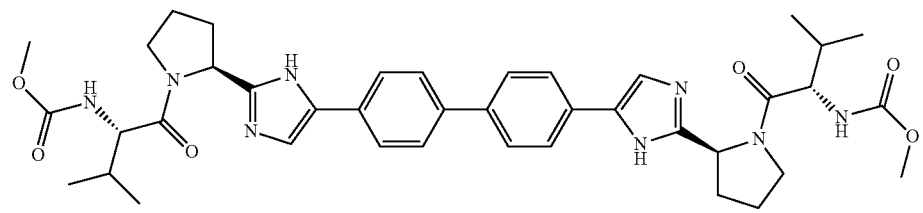

A solution of compound of formula 7 dissolved in DMF (0.017 M) was mixed with DIPEA (5.5 eq.) base and charged in one syringe. In another syringe solution of MOC-L-valine (0.057 M in DMF), EDC.HCl (2.5 equiv.), and HOBt (2.5 equiv.) were introduced into the capillary microreactor with a T-mixer using two separate syringe pumps. The two solutions were introduced to a T-mixer in a flow rate with the ratio of 1:3.3 (formula 7: Moc-L-valine) to maintain the stoichiometry, and then passed through a PTFE tubing (id=1000 μm, 1=12.8 m, vol.=10 ml) for the acid amine coupling during 50 min of residence time and 25° C. temperature (Table 7, entry 1). The resulting solution was charged with 30 mL cold water. After cooling to 20° C., 50 mL of ethyl acetate was added. The biphasic solution was filtered and the mixture split. The rich organic phase was washed with 2×40 mL sat (NaCl solution). The resulting hazy solution was cooled to 20° C. and filtered. The product was dried under vacuum at 50° C. to give ~94% of LC-MS yield of formula I.

Spectral data:

$^1$H NMR (500 MHz, DMSO) δ 15.35 (s, 1H), 14.87 (s, 1H), 8.17 (s, 1H), 8.04 (d, J=7.9 Hz, 2H), 7.94 (d, J=7.9 Hz, 2H), 7.28 (d, J=8.2 Hz, 1H), 5.22 (t, J=6.6 Hz, 1H), 4.14 (t, J=7.5 Hz, 1H), 4.03 (d, J=6.4 Hz, 1H), 3.84 (s, 1H), 3.55 (s, 3H), 3.43 (d, J=31.9 Hz, 1H), 2.38 (d, J=6.1 Hz, 1H), 2.20 (s, 2H), 2.11 (dd, J=14.3, 7.8 Hz, 1H), 2.06-1.91 (m, 1H), 0.85 (d, J=6.6 Hz, 3H), 0.77 (d, J=6.6 Hz, 3H).

$^{13}$C NMR (126 MHz, DMSO) δ 171.48 (s), 157.44 (s), 149.83 (s), 139.64 (s),132.20, 127.66 (s), 127.00, 126.35 (s), 115.53 (s), 58.38 (s), 53.33 (s), 52.02 (s), 47.68 (s), 31.54 (s), 29.45 (s), 25.39 (s), 20.05 (s), 18.23 (s).

IR ($v_{max}$): 3379, 2963, 2827, 2655, 1724, 1642, 1524, 1434, 1355, 1312, 1240, 1197, 1101, 1024 cm$^{-1}$ MS (EI): found: 738.39 (M$^+$).

Advantages of the Invention

The present invention amalgamates electrochemistry and microfluidics to develop a unique ultra-fast, continuous micro-electro-flow process for oxidant free C—C bond formation using micro-patterned anode capable of activating even less reactive substrates resulting in efficient reactions (for example symmetrical biaryl synthesis was achieved using continuous micro-electro-flow reactor containing Ni@Cu or Pt@Ni@Cu electro-patterned anode materials within 4-200 min). In comparison the batch processes reactions are time consuming and less efficient in terms of product yield.

The present invention further relates to the said process for daclatasvir synthesis in 138 min. time with improved overall yield (in general daclatasvir synthesis need 10 days' time through routine synthetic protocols in batch process).

The additional plug and play and electro-plating research ultimately enables the continuous synthesis of modern small molecule pharmaceuticals, including enantiopure active pharmaceutical ingredients to fill future gap for quick manufacturing of the late stage functionalized biological active compounds.

The present invention presents an appealing alternative to traditional, toxic redox-based methods by offering safer, sustainable and less wastage route to C—C bond formation.

We claim:

1. A continuous flow process for preparation of daclatasvir of Formula I, comprising the steps of:

Formula I

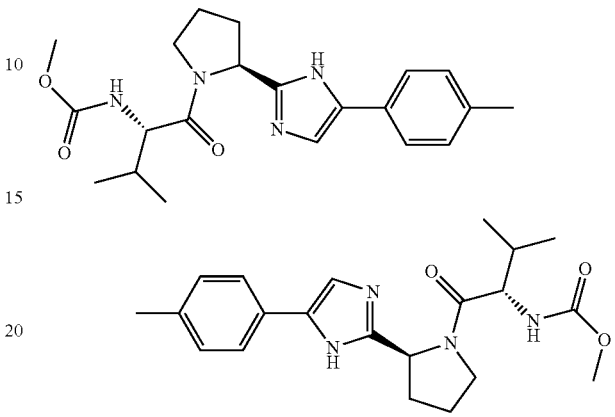

a) introducing a solution of a haloarene of Formula 1 and a Ni catalyst of Formula 2 in an aprotic solvent to a continuous micro-electro-flow reactor and maintaining a reaction mixture in the reactor for about 1-200 minutes at a temperature of about 25-80° C. and at a pressure of about 0-5 bar to obtain compounds of Formula 3a-3h;

Formula 1

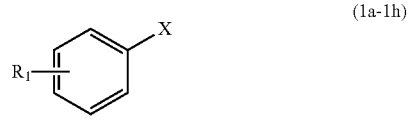

(1a-1h)

Formula 2

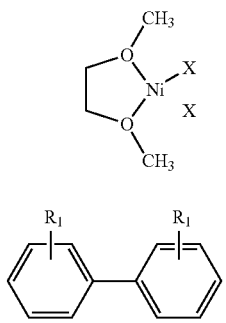

(3a-3h)

wherein compounds of Formula 1 are independently selected from the group: bromobenzene (1a); chlorobenzene (1a'); 1-bromo-4-methylbenzene (1b); 1-chloro-4-methylbenzene (1b'); 1-bromo-3-methylbenzene (1c); 1-chloro-3-methylbenzene (1c'); 1-bromonaphthalene (1d); 1-chloronaphthalene (1d'); 2-bromonaphthalene (1e); 2-chloronaphthalene (1e'); 4-bromo-1,1'-biphenyl (1f); 4-chloro-1,1'-biphenyl (1f'); 2-(4-bromophenyl)-2-methyl-1,3-dioxolane (1g); 1-(4-bromophenyl) ethanone (1h);

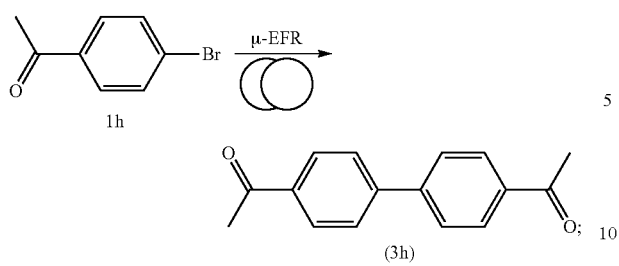

(3h)

b) continuous flow bromination of the compound of Formula 3h obtained in step a) by reacting with a brominating agent in an aprotic solvent while maintaining a reaction mixture in the reactor for about 10-200 minutes at a temperature of about 30-50° C. and at a pressure of about 1-10 bar to obtain a compound of Formula 4;

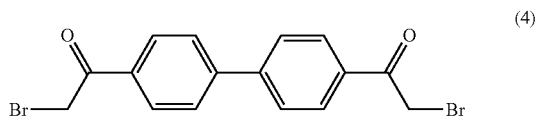

c) reaction of the compound of formula 4 obtained in step b) with N-protected-L-proline in an aprotic solvent while maintaining a reaction mixture in the reactor for about 1-5 minutes at a temperature of about 30-80° C. and at a pressure of about 1-10 bar to obtain a compound of formula 5;

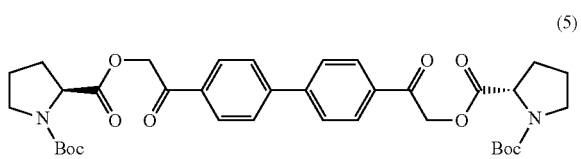 [SMILES: CC(C)(C)OC(=O)N1CCC[C@H]1C(=O)OCC(=O)c1ccc(-c2ccc(C(=O)COC(=O)[C@@H]3CCCN3C(=O)OC(C)(C)C)cc2)cc1]

d) reaction of the compound of formula 5 obtained in step c) with a regent while maintaining a reaction mixture in the reactor for about 1-5 minutes at a temperature of about 130-180° C. and at a pressure of about 10-30 bar to obtain a compound of formula 6;

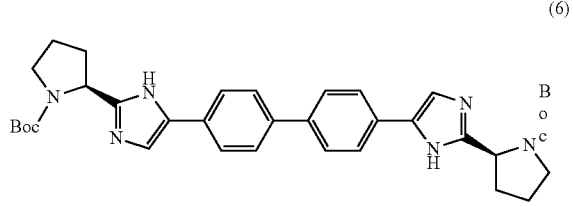 [SMILES: CC(C)(C)OC(=O)N1CCC[C@H]1c1ncc(-c2ccc(-c3ccc(-c4cnc([C@@H]5CCCN5)[nH]4)cc3)cc2)[nH]1]

e) deprotection of the compound of formula 6 obtained in step d) by reacting it with aqueous HCl in a protic solvent while maintaining a reaction mixture in the reactor for about 1-5 minutes at a temperature of about 20-40° C. and at a pressure of about 1-10 bar to obtain a compound of formula 7;

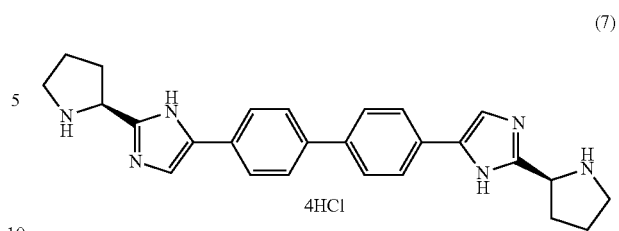

f) coupling of the compound of formula 7 or its pharmaceutically acceptable salt obtained in step e) with N-Moc-L-valine while maintaining a reaction mixture in the reactor for about 20-100 minutes at a temperature of about 20-40° C. and at a pressure of about 1-10 bar to obtain daclatasvir of formula I.

2. The process as claimed in claim 1, wherein the continuous micro-electro-flow reactor comprising of a copper plate anode support micro-patterned with inorganic nanoparticles; wherein, the inorganic nanoparticles comprise nickel nanoparticles, platinum nanoparticles or a combination thereof, wherein, the inorganic nanoparticles (Ni, Pt@Ni) have an average size in the range of 10-100 nm and a electroplated thickness of 4-100 μM.

3. The process as claimed in claim 1, wherein in step a) a reacting compound of formula 1 reacts with a compound of formula 2 in presence of various combinations of electrodes, wherein, the electrode is selected from the group consisting of Ni@Cu, Pt@Ni@Cu, Graphite, and Cu.

4. The process as claimed in claim 1, wherein in bromination step b) the compound of formula 3h reacts with brominating agent in presence of a Lewis acid and solvent, wherein, the brominating agent is selected from the group consisting of bromine, boron tribromide, phosphorus tribromide, carbon tetrabromide, N-bromoacetamide, N-bromophthalimide, N-bromosuccinimide, bromotrichloromethane, pyridinium tribromide, tetrabutylammonium tribromide, trimethylphenylammonium tribromide, benzyltrimethyl ammoniumtribromide, bromodimethylsulfonium bromide, 1-butyl-3-methylimidazolium tribromide, 1, 2-dibromo-1, 1, 2, 2-tetrachloroethane, 4-dimethylaminopyridinium bromide, 2, 4, 4, 6-tetrabromo-2, 5-cyclohexadienone, and mixtures thereof; and the Lewis acid is selected from the group consisting of $BF_3$, $MgBr_2$, $SnCl_4$, $TiCl_4$, $FeCl_3$, $AlCl_3$, $MeAlCl_2$, $Me_2AlCl$, $LiClO_4$, and mixtures thereof.

5. The process as claimed in claim 1, wherein in steps a), b) and c) the solvent is a polar aprotic solvent selected from the group consisting of acetonitrile, dichloromethane, dichloroethane, tetrahydrofuran, ethyl acetate, isopropyl acetate, dimethylformamide, dimethyl sulfoxide, acetone, N-Methylpyrrolidone, and mixtures thereof.

6. The process as claimed in claim 1, wherein in the step c) reaction of the compound of formula 4 with N-Protected-L-proline is performed in presence of a base and a solvent, wherein, the base is selected from the group consisting of trimethylamine, sodium hydroxide, potassium hydroxide, sodium methoxide, sodium tert-butoxide, potassium tert-butoxide, sodium carbonate, potassium carbonate, cesium carbonate, sodium bicarbonate, potassium bicarbonate, triethylamine, isopropyl ethylamine, diisopropyl amine, diisopropyl ethylamine, N-methyl morpholine, piperidine, pyridine and mixtures thereof.

7. The process as claimed in claim 1, wherein in step d) reaction of the compound of formula 5 with the reagent occurs in presence of a base and a solvent, wherein, the reagent is selected from the group consisting of ammonium acetate, ammonium formate, ammonium sulfamate, ammonium phosphate, ammonium citrate, ammonium carbamate, ammonia, and mixtures thereof.

8. The process as claimed in claim 1, wherein in deprotection step e) reaction of the compound of formula 6 is carried out using a deprotecting agent in presence of a solvent, wherein, the deprotecting agent is selected from the group consisting of HCl, $H_2SO_4$, $HNO_3$, trimethylsilyl iodide, and mixtures thereof and the solvent is selected from the group consisting of alcohol, ester, and mixtures thereof.

9. The process as claimed in claim 1, wherein, in coupling step f) the compound of formula 7 is reacted with N-Moc-L-valine in presence of a coupling agent, a base, and a solvent, wherein, the coupling agent is selected from the group consisting of 1,1'-carbonyldiimidazole, bis(2-oxo-3-oxazolidinyl)phosphinic chloride, 1-hydroxy-7-azabenzotriazole, 1-hydroxybenzotriazole hydrate, 3-hydroxyl-2,3-benzotriazin-4(3H)-one, 1-(3-dimethyaminopropyl)-3-ethylcarbodiimide hydrochloride, 4-nitrophenol, pentafluorophenol, 2-hydroxypyridine, N-hydroxysuccinimide, N-hydroxyphthalamide, 2-mercaptobenzoxazole, trimethylacetyl chloride, isobutylchloroformate, chlorodimethoxytriazole, oxalyl chloride, 2-hydroxypyridine-N-oxide, 5-nitro-2-hydroxypyridine, Boc-L-valine anhydride, and mixtures thereof.

10. The process as claimed in claim 1, wherein, the continuous flow process system is employed for bulk scale preparation of daclatasvir (formula I).

\* \* \* \* \*